United States Patent
Smith et al.

(10) Patent No.: US 11,918,442 B2
(45) Date of Patent: Mar. 5, 2024

(54) GARMENT-LIKE ABSORBENT ARTICLES

(71) Applicant: The Procter & Gamble Company, Cincinnati, OH (US)

(72) Inventors: Alizha V. Smith, Wyoming, OH (US); Christopher S. Cameron, Cincinnati, OH (US); Nayda Liz Ramos Medina, Cincinnati, OH (US); Vanessa M. Melendez, Cincinnati, OH (US); Brittany D. Canfield, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 447 days.

(21) Appl. No.: 16/575,424

(22) Filed: Sep. 19, 2019

(65) Prior Publication Data
US 2020/0100955 A1  Apr. 2, 2020

Related U.S. Application Data

(60) Provisional application No. 62/821,485, filed on Mar. 21, 2019, provisional application No. 62/737,367, filed on Sep. 27, 2018.

(51) Int. Cl.
*A61F 13/511* (2006.01)
*A61F 13/15* (2006.01)
(Continued)

(52) U.S. Cl.
CPC ........ *A61F 13/15585* (2013.01); *A61F 13/49* (2013.01); *A61F 13/51104* (2013.01);
(Continued)

(58) Field of Classification Search
CPC ................ A61F 13/49; A61F 13/51104; A61F 13/5126; A61F 13/51401; A61F 13/51476;
(Continued)

(56) References Cited

U.S. PATENT DOCUMENTS

| 4,333,979 A | 6/1982 | Sciaraffa et al. |
| 4,451,520 A | 5/1984 | Tecl et al. |

(Continued)

FOREIGN PATENT DOCUMENTS

| CN | 1685099 | 10/2005 |
| CN | 101208063 A | 6/2008 |

(Continued)

OTHER PUBLICATIONS

All Office Actions, U.S. Appl. No. 16/575,684.
(Continued)

*Primary Examiner* — Jessica Arble
(74) *Attorney, Agent, or Firm* — Amanda Herman Berghauer; Christian Michael Best

(57) ABSTRACT

Garment-like absorbent articles are disclosed. The garment-like absorbent articles may include one or more nonwoven components that having repeating patterns of apertures and/or bonds. The nonwoven components may also have certain repeat unit areas, repeat unit width, and repeat unit lengths to aid in softness and to provide improved aesthetic appearance to consumers.

15 Claims, 30 Drawing Sheets

(51) Int. Cl.

| | |
|---|---|
| *A61F 13/49* | (2006.01) |
| *A61F 13/512* | (2006.01) |
| *A61F 13/514* | (2006.01) |
| *D04H 3/16* | (2006.01) |
| *A61F 13/84* | (2006.01) |
| *B32B 5/02* | (2006.01) |
| *B32B 7/02* | (2019.01) |
| *B32B 7/12* | (2006.01) |

(52) U.S. Cl.
CPC .... *A61F 13/5126* (2013.01); *A61F 13/51401* (2013.01); *A61F 13/51476* (2013.01); *A61F 13/51496* (2013.01); *D04H 3/16* (2013.01); *A61F 2013/51178* (2013.01); *A61F 2013/5127* (2013.01); *A61F 2013/51452* (2013.01); *A61F 2013/51486* (2013.01); *A61F 2013/8497* (2013.01); *B32B 5/022* (2013.01); *B32B 7/02* (2013.01); *B32B 7/12* (2013.01); *B32B 2307/7265* (2013.01); *B32B 2555/02* (2013.01)

(58) Field of Classification Search
CPC ...... A61F 13/51496; A61F 2013/51178; A61F 2013/5127; A61F 2013/51452
See application file for complete search history.

(56) References Cited

U.S. PATENT DOCUMENTS

| | | |
|---|---|---|
| 4,741,941 A | 5/1988 | Englebert et al. |
| 4,970,104 A | 11/1990 | Radwanski |
| 5,180,534 A | 1/1993 | Thomas et al. |
| 5,188,649 A | 2/1993 | Macedo et al. |
| 5,230,851 A | 7/1993 | Thomas |
| 5,254,194 A | 10/1993 | Ott et al. |
| 5,256,231 A | 10/1993 | Gorman et al. |
| 5,318,741 A | 6/1994 | Thomas |
| 5,326,612 A | 7/1994 | Goulait et al. |
| 5,334,289 A | 8/1994 | Trokhan et al. |
| 5,340,372 A | 8/1994 | Macedo et al. |
| 5,354,591 A | 10/1994 | Ott et al. |
| 5,389,470 A | 2/1995 | Parker et al. |
| 5,407,439 A | 4/1995 | Goulait et al. |
| 5,470,417 A | 11/1995 | Goulait |
| 5,514,523 A | 5/1996 | Trokhan et al. |
| 5,540,673 A | 7/1996 | Thomas et al. |
| 5,547,531 A | 8/1996 | Allen et al. |
| 5,569,233 A | 10/1996 | Goulait |
| 5,575,874 A | 11/1996 | Griesbach et al. |
| 5,595,567 A | 1/1997 | King et al. |
| 5,599,420 A | 2/1997 | Yeo et al. |
| 5,605,729 A | 2/1997 | Mody et al. |
| 5,610,511 A | 3/1997 | Parker |
| 5,611,791 A | 3/1997 | Gorman et al. |
| 5,614,281 A | 3/1997 | Jackson et al. |
| 5,615,460 A | 4/1997 | Weirich et al. |
| 5,616,394 A | 4/1997 | Gorman et al. |
| 5,628,097 A | 5/1997 | Benson et al. |
| 5,643,397 A | 7/1997 | Gorman et al. |
| 5,643,653 A | 7/1997 | Griesbach, III et al. |
| 5,647,864 A | 7/1997 | Allen et al. |
| 5,699,593 A | 12/1997 | Jackson |
| 5,714,107 A | 2/1998 | Levy et al. |
| 5,725,927 A | 3/1998 | Zilg et al. |
| 5,762,645 A | 6/1998 | Peck et al. |
| 5,773,120 A | 6/1998 | Deka et al. |
| 5,817,394 A | 10/1998 | Alikhan et al. |
| 5,825,174 A | 10/1998 | Parker |
| 5,830,298 A | 11/1998 | Jackson |
| 5,858,504 A | 1/1999 | Steven |
| 5,858,515 A | 1/1999 | Stokes et al. |
| 5,888,607 A | 3/1999 | Seth et al. |
| 5,895,623 A | 4/1999 | Trokhan et al. |
| 5,916,661 A | 6/1999 | Benson et al. |
| 5,964,742 A | 10/1999 | Mccormack et al. |
| 5,997,981 A | 12/1999 | Mccormack et al. |
| D428,267 S | 7/2000 | Sayovitz et al. |
| 6,139,941 A | 10/2000 | Jankevics et al. |
| 6,140,551 A | 10/2000 | Niemeyer et al. |
| 6,150,002 A | 11/2000 | Varona |
| 6,162,522 A | 12/2000 | Deka et al. |
| 6,197,404 B1 | 3/2001 | Varona |
| 6,238,767 B1 | 5/2001 | Mccormack et al. |
| 6,319,455 B1 | 11/2001 | Kauschke et al. |
| 6,331,268 B1 | 12/2001 | Kauschke et al. |
| 6,331,345 B1 | 12/2001 | Kauschke et al. |
| 6,361,638 B2 | 3/2002 | Takai et al. |
| 6,383,431 B1 | 5/2002 | Dobrin et al. |
| 6,395,957 B1 | 5/2002 | Chen et al. |
| 6,436,512 B1 | 8/2002 | Kauschke et al. |
| 6,589,638 B1 | 7/2003 | Mccormack et al. |
| 6,592,697 B2 | 7/2003 | Pike et al. |
| 6,623,469 B1 | 9/2003 | Thomas |
| 6,632,504 B1 | 10/2003 | Gillespie et al. |
| 6,637,079 B1 | 10/2003 | Goulait et al. |
| 6,673,418 B1 | 1/2004 | DeOlivera et al. |
| 6,743,321 B2 | 6/2004 | Guralski et al. |
| 6,756,327 B2 | 6/2004 | Martin |
| 6,818,802 B2 | 11/2004 | Takai et al. |
| 6,838,154 B1 | 1/2005 | Varona et al. |
| 6,849,142 B1 | 2/2005 | Goulait et al. |
| 6,921,570 B2 | 7/2005 | Belau et al. |
| 6,955,668 B2 | 10/2005 | Imberg et al. |
| 6,969,377 B2 | 11/2005 | Koele et al. |
| 7,156,937 B2 | 1/2007 | Provost et al. |
| 7,162,749 B2 | 1/2007 | Carbone et al. |
| 7,207,979 B2 | 4/2007 | Price et al. |
| 7,276,642 B2 | 10/2007 | Belau |
| 7,371,919 B1 | 5/2008 | Busam et al. |
| 7,407,496 B2 | 8/2008 | Petersen |
| 7,465,366 B2 | 12/2008 | Provost et al. |
| 7,497,851 B2 | 3/2009 | Koele et al. |
| 7,507,463 B2 | 3/2009 | Noda et al. |
| 7,544,628 B2 | 6/2009 | Stupperich et al. |
| 7,547,469 B2 | 6/2009 | Provost |
| 7,553,535 B2 | 6/2009 | Noda et al. |
| 7,562,426 B2 | 7/2009 | Barker et al. |
| 7,662,462 B2 | 2/2010 | Noda et al. |
| 7,789,870 B2 | 9/2010 | Horn et al. |
| 7,790,264 B2 | 9/2010 | Lester, Jr. et al. |
| 7,805,818 B2 | 10/2010 | Horn et al. |
| 7,862,550 B2 | 1/2011 | Koele et al. |
| 7,895,718 B2 | 3/2011 | Horn |
| 7,897,240 B2 | 3/2011 | Noda et al. |
| 7,954,213 B2 | 6/2011 | Mizutani |
| 7,955,549 B2 | 6/2011 | Noda et al. |
| 7,960,008 B2 | 6/2011 | Lester, Jr. et al. |
| 7,968,479 B2 | 6/2011 | Welch et al. |
| 7,981,822 B2 | 7/2011 | Lester, Jr. et al. |
| 8,002,761 B2 | 8/2011 | Utsunomiya et al. |
| 8,034,431 B2 | 10/2011 | Seth |
| 8,123,734 B2 | 2/2012 | Imberg |
| 8,143,177 B2 | 3/2012 | Noda et al. |
| 8,183,431 B2 | 5/2012 | Noda et al. |
| 8,212,103 B2 | 7/2012 | Kingsford et al. |
| 8,257,333 B2 | 9/2012 | Hancock-Cooke |
| 8,273,941 B2 | 9/2012 | Uematsu et al. |
| 8,304,600 B2 | 11/2012 | Noda et al. |
| 8,323,435 B2 | 12/2012 | Durrance et al. |
| 8,388,596 B2 | 3/2013 | Horn |
| 8,426,672 B2 | 4/2013 | Kingsford et al. |
| 8,562,580 B2 | 10/2013 | Van Gompel et al. |
| 8,574,209 B2 | 11/2013 | Nishitani et al. |
| 8,585,666 B2 | 11/2013 | Weisman et al. |
| 8,590,119 B2 | 11/2013 | Horn |
| 8,673,097 B2 | 3/2014 | Barker et al. |
| RE44,842 E | 4/2014 | Lester, Jr. et al. |
| 8,753,459 B2 | 6/2014 | Provost |
| 8,758,569 B2 | 6/2014 | Aberg et al. |
| 8,853,108 B2 | 10/2014 | Ahoniemi et al. |
| 8,865,965 B2 | 10/2014 | Sato et al. |
| 8,898,868 B2 | 12/2014 | Horn et al. |
| 8,906,275 B2 | 12/2014 | Davis et al. |
| 9,056,032 B2 | 6/2015 | Ashraf et al. |

(56) References Cited

U.S. PATENT DOCUMENTS

| | | |
|---|---|---|
| 9,078,793 B2 | 7/2015 | Barker |
| 9,084,701 B2 | 7/2015 | Ramos Medina et al. |
| 9,091,005 B2 | 7/2015 | Masuda et al. |
| 9,095,477 B2 | 8/2015 | Yamaguchi et al. |
| 9,114,045 B2 | 8/2015 | Sakaguchi et al. |
| 9,125,775 B2 | 9/2015 | Durrance et al. |
| 9,156,229 B2 | 10/2015 | Noda et al. |
| 9,205,005 B2 | 12/2015 | Kikuchi et al. |
| 9,205,006 B2 | 12/2015 | Cheng et al. |
| 9,259,059 B2 | 2/2016 | Horn et al. |
| 9,259,367 B2 | 2/2016 | Magee et al. |
| RE45,946 E | 3/2016 | Lester, Jr. et al. |
| 9,408,761 B2 | 8/2016 | Xu |
| 9,453,303 B2 | 9/2016 | Aberg et al. |
| 9,468,265 B2 | 10/2016 | Horn |
| D772,583 S | 11/2016 | Hannen et al. |
| 9,504,610 B2 | 11/2016 | Cheng et al. |
| 9,662,248 B2 | 5/2017 | Van Gompel et al. |
| 9,732,454 B2 | 8/2017 | Davis et al. |
| 9,737,441 B2 | 8/2017 | Song et al. |
| 9,744,085 B2 | 8/2017 | Ashraf et al. |
| 9,877,876 B2 | 1/2018 | Huang et al. |
| 9,903,070 B2 | 2/2018 | Mourad et al. |
| 9,913,764 B2 | 3/2018 | Thomas et al. |
| 9,974,700 B2 | 5/2018 | Cheng et al. |
| 10,016,316 B2 | 7/2018 | Sakaguchi et al. |
| 10,016,319 B2 | 7/2018 | Cheng et al. |
| 10,028,866 B2 | 7/2018 | Xu |
| 10,190,244 B2 | 1/2019 | Ashraf et al. |
| 2001/0008683 A1 | 7/2001 | Takai et al. |
| 2001/0029141 A1 | 10/2001 | Mizutani |
| 2002/0103469 A1 | 8/2002 | Chen et al. |
| 2002/0150431 A1 | 10/2002 | Ofosu-Asante |
| 2002/0153271 A1 | 10/2002 | McManus et al. |
| 2002/0193032 A1 | 12/2002 | Newkirk et al. |
| 2003/0077430 A1 | 4/2003 | Grimm |
| 2003/0093045 A1 | 5/2003 | Jensen |
| 2003/0116259 A1 | 6/2003 | Sayovitz et al. |
| 2003/0119404 A1 | 6/2003 | Belau et al. |
| 2003/0125687 A1 | 7/2003 | Gubernick et al. |
| 2003/0203162 A1 | 10/2003 | Christopher et al. |
| 2003/0203691 A1 | 10/2003 | Fenwick et al. |
| 2003/0211802 A1 | 11/2003 | Keck et al. |
| 2004/0059309 A1 | 3/2004 | Nortman |
| 2004/0063369 A1 | 4/2004 | Ahn et al. |
| 2004/0158957 A1 | 8/2004 | Horn et al. |
| 2004/0193135 A1 | 9/2004 | Van Gompel |
| 2004/0230171 A1 | 11/2004 | Ando |
| 2005/0147785 A1 | 7/2005 | Ahn et al. |
| 2005/0148971 A1 | 7/2005 | Kuroda et al. |
| 2005/0196580 A1 | 9/2005 | Provost |
| 2005/0196583 A1 | 9/2005 | Provost |
| 2005/0217092 A1 | 10/2005 | Barker et al. |
| 2006/0019055 A1 | 1/2006 | Lester et al. |
| 2006/0021536 A1 | 2/2006 | Song et al. |
| 2006/0080810 A1 | 4/2006 | Horn et al. |
| 2006/0087053 A1 | 4/2006 | O'Donnell et al. |
| 2006/0105075 A1 | 5/2006 | Otsubo |
| 2006/0189954 A1 | 8/2006 | Kudo et al. |
| 2006/0286343 A1 | 12/2006 | Curro et al. |
| 2007/0026753 A1 | 2/2007 | Neely et al. |
| 2007/0045143 A1 | 3/2007 | Clough et al. |
| 2007/0045144 A1 | 3/2007 | Wheeler et al. |
| 2007/0049889 A1 | 3/2007 | Larson et al. |
| 2007/0128411 A1 | 6/2007 | Kawai et al. |
| 2007/0178273 A1 | 8/2007 | Provost et al. |
| 2007/0179466 A1 | 8/2007 | Tremblay et al. |
| 2007/0298214 A1 | 12/2007 | Noda et al. |
| 2007/0298667 A1 | 12/2007 | Noda et al. |
| 2008/0086104 A1 | 4/2008 | Karlsson |
| 2008/0102725 A1 | 5/2008 | Lacey et al. |
| 2008/0108967 A1 | 5/2008 | Muzushima et al. |
| 2008/0149292 A1 | 6/2008 | Scherb |
| 2008/0161765 A1 | 7/2008 | Morman et al. |
| 2009/0169827 A1 | 7/2009 | Dharmadhikary et al. |
| 2009/0240222 A1 | 9/2009 | Tomoko et al. |
| 2009/0280274 A1 | 11/2009 | Herlein |
| 2010/0030176 A1* | 2/2010 | Beckert .............. A61F 13/622 |
| | | 604/389 |
| 2010/0036346 A1 | 2/2010 | Hammons |
| 2010/0036349 A1 | 2/2010 | Hammons |
| 2010/0048072 A1 | 2/2010 | Kauschke |
| 2010/0286644 A1 | 11/2010 | Li |
| 2010/0298796 A1 | 11/2010 | Horn |
| 2010/0324517 A1 | 12/2010 | Lenhult et al. |
| 2011/0250378 A1 | 10/2011 | Eaton et al. |
| 2011/0250413 A1 | 10/2011 | Lu et al. |
| 2011/0257620 A1 | 10/2011 | Horn et al. |
| 2011/0313385 A1 | 12/2011 | Hammons et al. |
| 2012/0004633 A1 | 1/2012 | Marcelo et al. |
| 2012/0022488 A1 | 1/2012 | Otsubo et al. |
| 2012/0029454 A1 | 2/2012 | Li et al. |
| 2012/0089112 A1 | 4/2012 | Horn et al. |
| 2012/0095429 A1 | 4/2012 | Kobayashi |
| 2012/0095431 A1 | 4/2012 | Tsai |
| 2012/0177886 A1 | 7/2012 | Kanya |
| 2012/0189814 A1 | 7/2012 | Coslett et al. |
| 2012/0196091 A1 | 8/2012 | Mizutani et al. |
| 2012/0226249 A1 | 9/2012 | Prodoehl et al. |
| 2012/0231206 A1 | 9/2012 | Thompson, Jr. et al. |
| 2012/0315440 A1 | 12/2012 | Ichikawa et al. |
| 2012/0316532 A1 | 12/2012 | Mccormick |
| 2013/0112584 A1 | 5/2013 | Gaspari et al. |
| 2013/0138073 A1 | 5/2013 | Horn et al. |
| 2013/0139960 A1 | 6/2013 | Maruyama et al. |
| 2013/0171421 A1 | 7/2013 | Weisman et al. |
| 2013/0310797 A1* | 11/2013 | Zink .............. A61F 13/49058 |
| | | 604/392 |
| 2013/0320584 A1 | 12/2013 | Davis et al. |
| 2014/0000070 A1 | 1/2014 | Ashraf et al. |
| 2014/0000784 A1* | 1/2014 | Rane .............. D04H 13/00 |
| | | 156/62.8 |
| 2014/0037906 A1 | 2/2014 | Polosa et al. |
| 2014/0039438 A1 | 2/2014 | Ferrer et al. |
| 2014/0044934 A1 | 2/2014 | Bills et al. |
| 2014/0127460 A1 | 5/2014 | Xu et al. |
| 2014/0234575 A1 | 8/2014 | Mitsuno et al. |
| 2014/0259483 A1 | 9/2014 | Cheng et al. |
| 2014/0272261 A1 | 9/2014 | Udengaard et al. |
| 2014/0272359 A1 | 9/2014 | Cheng et al. |
| 2014/0276517 A1 | 9/2014 | Chester et al. |
| 2014/0296815 A1 | 10/2014 | Takken et al. |
| 2014/0305570 A1 | 10/2014 | Matsunaga et al. |
| 2014/0324009 A1 | 10/2014 | Lee et al. |
| 2014/0343526 A1 | 11/2014 | Knapmeyer et al. |
| 2015/0038933 A1 | 2/2015 | Day et al. |
| 2015/0173967 A1 | 6/2015 | Kreuzer et al. |
| 2015/0182387 A1* | 7/2015 | Ferrer .............. A61F 13/51401 |
| | | 604/374 |
| 2015/0238373 A1 | 8/2015 | Ramos-Medina et al. |
| 2015/0250662 A1 | 9/2015 | Isele et al. |
| 2015/0250663 A1 | 9/2015 | Wagner et al. |
| 2015/0282999 A1 | 10/2015 | Arizti et al. |
| 2016/0007819 A1 | 1/2016 | Cheng et al. |
| 2016/0067119 A1 | 3/2016 | Weisman et al. |
| 2016/0101003 A1 | 4/2016 | Jennewein et al. |
| 2016/0106633 A1 | 4/2016 | Nagata et al. |
| 2016/0129661 A1 | 5/2016 | Arora et al. |
| 2016/0136009 A1 | 5/2016 | Weisman et al. |
| 2016/0270976 A1 | 9/2016 | Minoguchi et al. |
| 2016/0324698 A1 | 11/2016 | Xu et al. |
| 2016/0362825 A1 | 12/2016 | Novarino et al. |
| 2016/0367408 A1 | 12/2016 | Coslett et al. |
| 2017/0000663 A1 | 1/2017 | Xu et al. |
| 2017/0014280 A1 | 1/2017 | Moritani |
| 2017/0014281 A1 | 1/2017 | Xie et al. |
| 2017/0014291 A1 | 1/2017 | Kie et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith et al. |
| 2017/0121873 A1 | 5/2017 | Kimura et al. |
| 2017/0151101 A1 | 6/2017 | Isele et al. |
| 2017/0151103 A1* | 6/2017 | Bianchi .............. A61F 13/49 |

(56) References Cited

U.S. PATENT DOCUMENTS

| | | | |
|---|---|---|---|
| 2017/0191198 A1 | 7/2017 | Ashraf et al. |
| 2017/0202318 A1 | 7/2017 | Morishita et al. |
| 2017/0246052 A1 | 8/2017 | Ludwig |
| 2017/0258650 A1 | 9/2017 | Rosati et al. |
| 2017/0281428 A1 | 10/2017 | Mueller et al. |
| 2017/0304123 A1 | 10/2017 | Ferrer et al. |
| 2017/0335498 A1 | 11/2017 | Hansen et al. |
| 2017/0348163 A1 | 12/2017 | Lakso et al. |
| 2018/0133070 A1 | 5/2018 | Thomas et al. |
| 2018/0168893 A1 | 6/2018 | Ashraf et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2018/0222143 A1 | 8/2018 | Gilbert et al. |
| 2018/0228659 A1* | 8/2018 | Conrad ............. A61F 13/51401 |
| 2018/0229216 A1 | 8/2018 | Smith et al. |
| 2018/0263830 A1 | 9/2018 | Uchida et al. |
| 2018/0281296 A1 | 10/2018 | Uchida et al. |
| 2019/0003079 A1 | 1/2019 | Ashraf et al. |
| 2019/0003080 A1 | 1/2019 | Ashraf et al. |
| 2019/0071802 A1 | 3/2019 | Novarino et al. |
| 2019/0112737 A1 | 4/2019 | Ashraf et al. |
| 2019/0161897 A1 | 5/2019 | Mecl et al. |
| 2019/0254882 A1 | 8/2019 | Trennepohl et al. |
| 2019/0290503 A1 | 9/2019 | Mullane et al. |
| 2020/0100949 A1 | 4/2020 | Smith et al. |
| 2020/0100956 A1 | 4/2020 | Ashraf et al. |
| 2020/0297555 A1 | 9/2020 | Ramos Medina et al. |

FOREIGN PATENT DOCUMENTS

| | | |
|---|---|---|
| CN | 101914838 A | 12/2010 |
| CN | 106943241 A | 7/2017 |
| EP | 0882828 A1 | 12/1998 |
| EP | 2660377 B1 | 4/2014 |
| JP | 2001-008713 | 1/2001 |
| JP | 2002-030559 | 1/2002 |
| JP | 2002165831 A | 6/2002 |
| JP | 2004-081254 | 3/2004 |
| JP | 2006-034872 | 2/2006 |
| JP | 2009-000512 | 1/2009 |
| JP | 2009-101091 | 5/2009 |
| JP | 2010-024573 | 2/2010 |
| JP | 2011-015707 | 1/2011 |
| JP | 2011137262 A | 7/2011 |
| JP | 2014-097257 | 5/2014 |
| JP | 2014094159 A | 5/2014 |
| JP | 2014-188042 | 10/2014 |
| JP | 2015112306 A | 6/2015 |
| WO | WO-9923905 | 5/1995 |
| WO | WO-9611107 | 4/1996 |
| WO | WO-9719808 | 6/1997 |
| WO | WO-2007096842 | 8/2007 |
| WO | 2012086730 A1 | 6/2012 |
| WO | 2013018846 A1 | 2/2013 |
| WO | WO-2003015681 | 2/2013 |
| WO | WO 2013084977 | 6/2013 |
| WO | 2013099625 A1 | 7/2013 |
| WO | 2013145966 A1 | 10/2013 |
| WO | WO-2014073637 | 9/2014 |
| WO | WO-2016001742 | 1/2016 |
| WO | WO-2016204131 | 12/2016 |
| WO | WO-2016204132 | 12/2016 |
| WO | WO-2017040240 | 3/2017 |
| WO | 2017110695 A1 | 6/2017 |
| WO | WO-2017105997 | 6/2017 |
| WO | 2017131597 A1 | 8/2017 |
| WO | WO-2017148865 | 9/2017 |
| WO | WO-2018124996 | 7/2018 |

OTHER PUBLICATIONS

All Office Actions, U.S. Appl. No. 16/575,706.
International Search Report and Written Opinion, PCT/US2019/051806, dated Dec. 6, 2019.
3D Nonwovens Developments for textured nonwovens; Sep. 19, 2017, pp. 1-2.
All Office Actions; U.S. Appl. No. 16/812,632.

* cited by examiner

GARMENT-LIKE ABSORBENT ARTICLES

CROSS REFERENCE TO RELATED APPLICATIONS

This application claims the benefit of U.S. Provisional Patent Application Ser. No. 62/737,367, filed on Sep. 27, 2018, and U.S. Provisional Patent Application No. 62/821,485, filed on Mar. 21, 2019, the entire disclosures of which are hereby incorporated by reference herein.

FIELD

The present disclosure is generally directed to garment-like absorbent articles and, is more particularly directed to, garment-like absorbent articles having aperture or bond patterns forming repeat units on one or more nonwoven components.

BACKGROUND

Absorbent articles are used to absorb and contain bodily exudates (e.g., urine, menses, and BM) in infants, children, and adults. Absorbent articles may comprise diapers, pants, adult incontinence products, and sanitary napkins, for example. The absorbent articles typically comprise a liquid permeable topsheet, a liquid impermeable backsheet, and an absorbent core positioned at least partially intermediate the topsheet and the backsheet. Various components of absorbent articles comprise nonwoven materials. Some examples are outer cover nonwoven materials, nonwoven ear materials, nonwoven landing zones, nonwoven topsheets, nonwoven leg cuff materials, and nonwoven belt materials. The nonwoven materials may have bond patterns to hold the fibers together, but that may appear of low quality and/or not customized. As such, nonwoven materials for absorbent articles should be improved.

SUMMARY

The present disclosure provides garment-like absorbent articles that overcome the disadvantages of current absorbent articles by providing absorbent articles with one or more nonwoven materials that have aperture and/or bond patterns formed by a plurality of repeat units. The repeat units should be of adequate repeat unit area, repeat unit width, and repeat unit length to make the nonwoven materials appear to be of high quality and/or customized. In some instances, it may be desirable to have an absorbent article with two different nonwoven materials with the same or similar patterns of bonds and/or apertures to reduce the modular appearance of current absorbent articles having quite different patterns of bonds on two different nonwoven components. The repeat units formed by the apertures and/or bond patterns may be the same, or substantially the same, on the same nonwoven component, and substantially similar or similar between the two or more different nonwoven components. The two or more nonwoven components may each have a high texture to promote softness and high quality. These features lead to a more garment-like and, thereby, higher quality impression of the absorbent articles by consumers. The patterns may be created by printing, embossing, bonding, and/or aperturing, for example.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Various non-limiting forms of the present disclosure will now be described to provide an overall understanding of the principles of the structure, function, manufacture, and use of the Garment-like Absorbent Articles disclosed herein. One or more examples of these non-limiting forms are illustrated in the accompanying drawings. Those of ordinary skill in the art will understand that the Garment-like Absorbent Articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

General Description of an Absorbent Article

Figure 1:
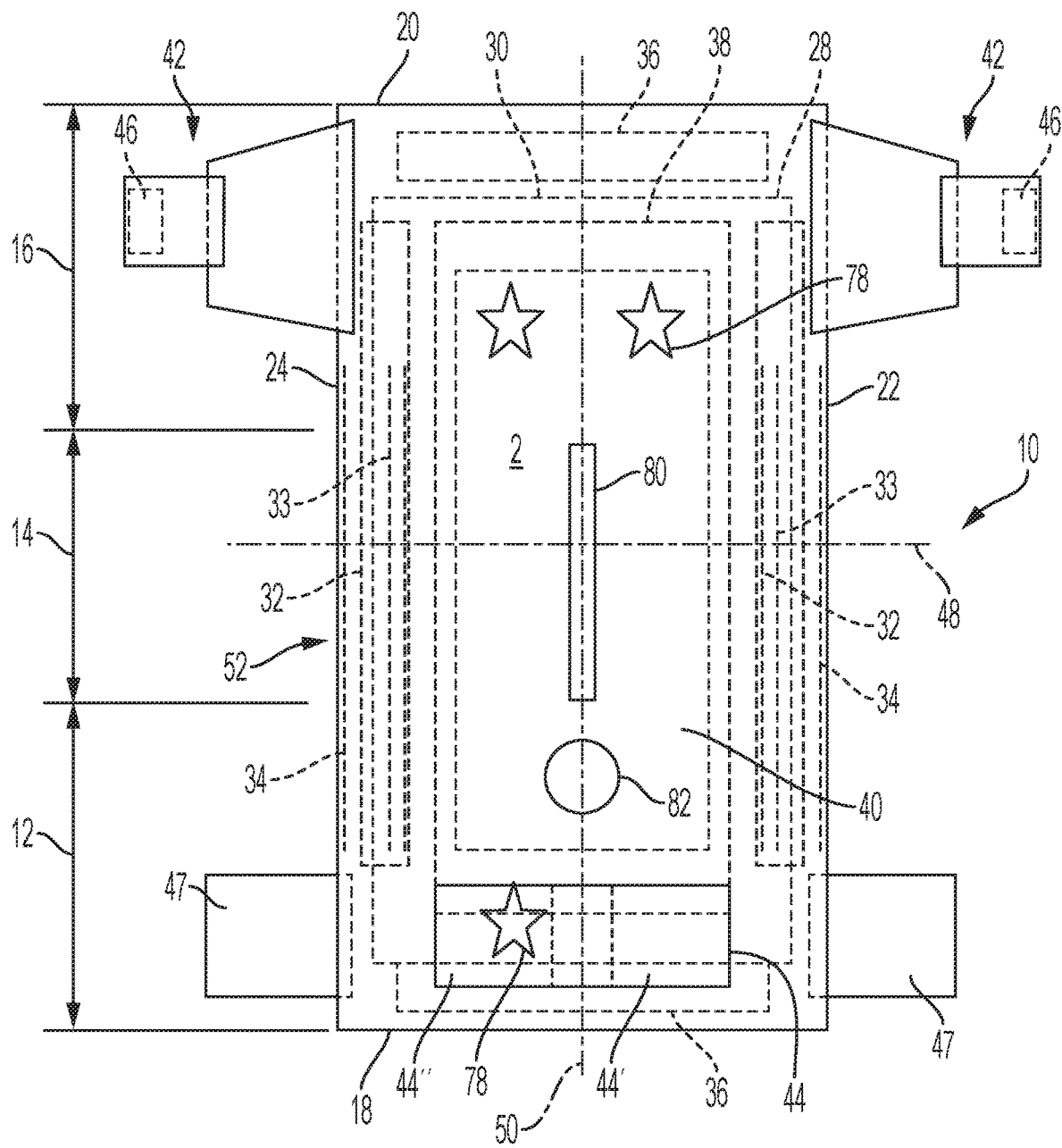
FIG. 1 is a plan view of an example absorbent article in the form of a taped diaper, garment-facing surface facing the viewer, in a flat laid-out state.
Figure 2:
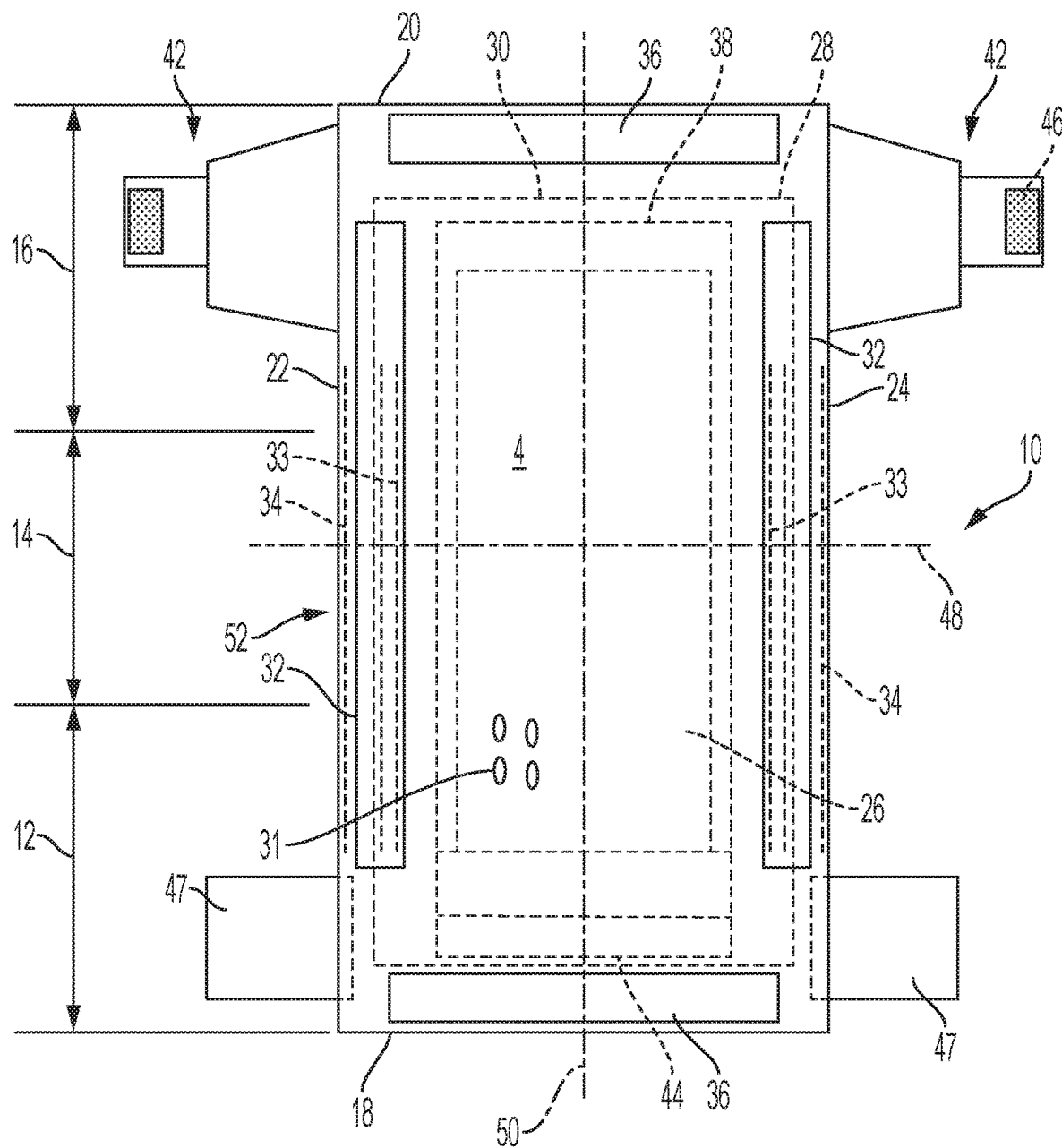
FIG. 2 is a plan view of the example absorbent article of FIG. 1, wearer-facing surface facing the viewer, in a flat laid-out state.
Figure 3:
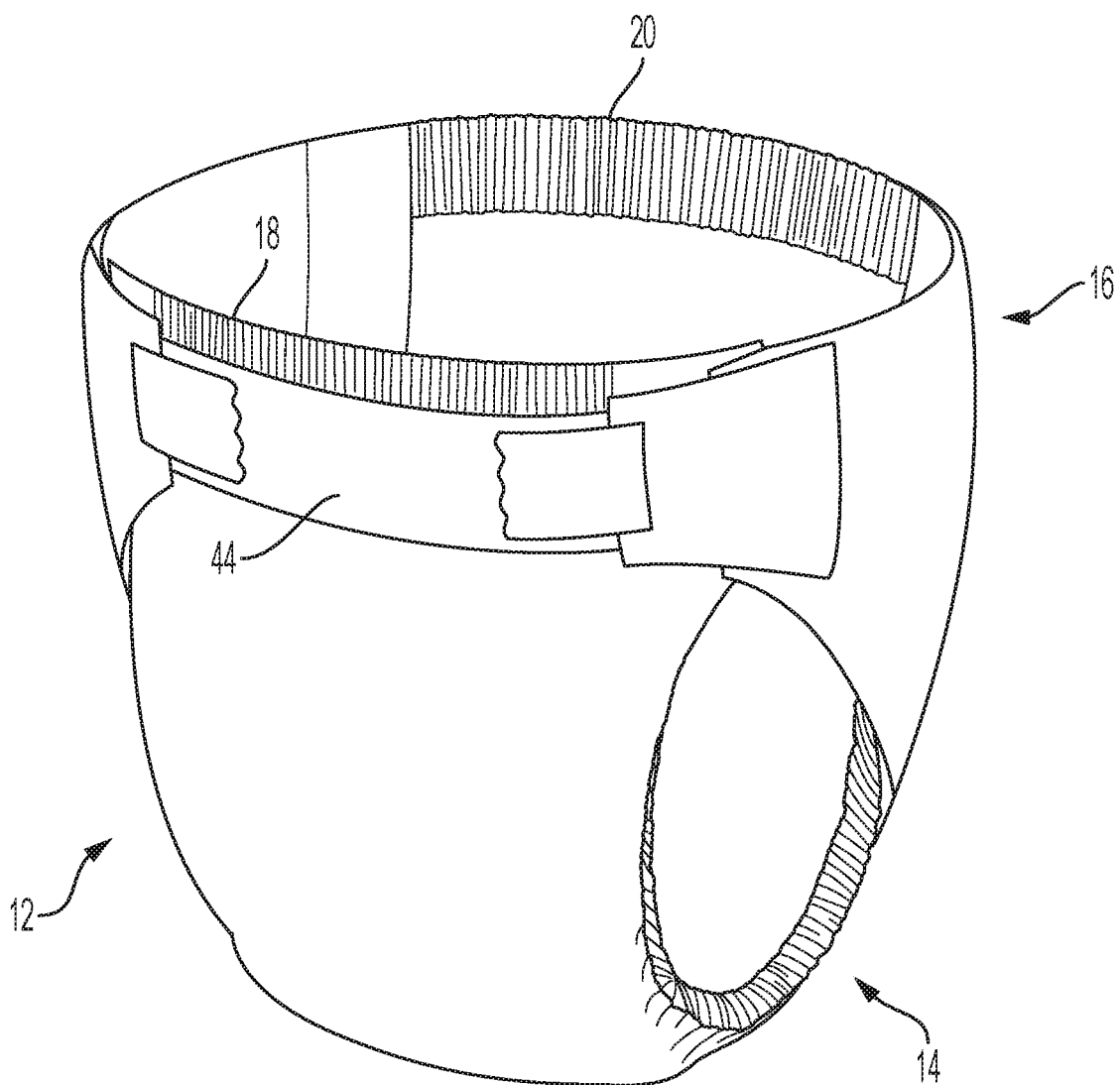
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 on tapes and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
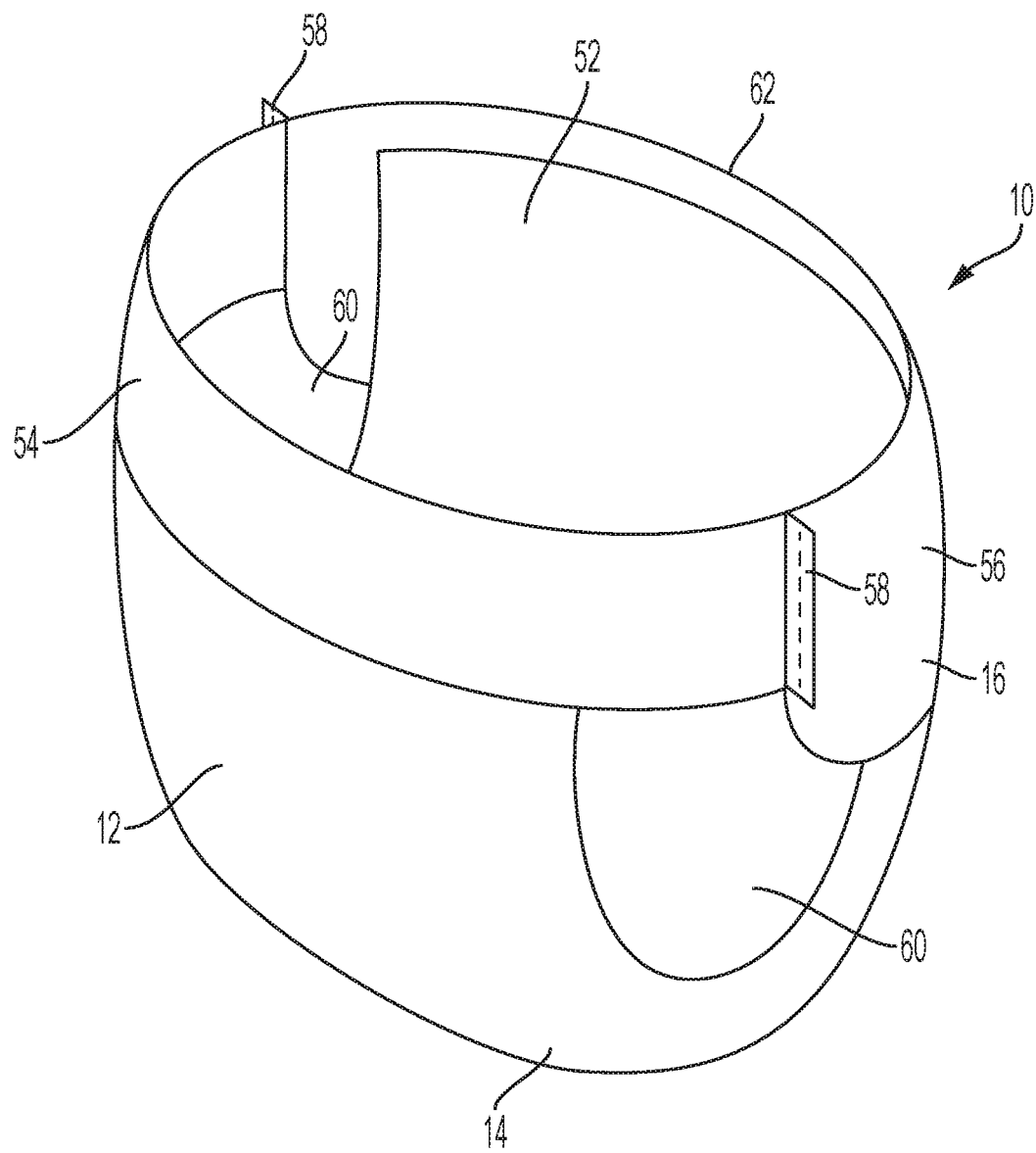
FIG. 4 is a front perspective view of an absorbent article in the form of a pant.
Figure 5:
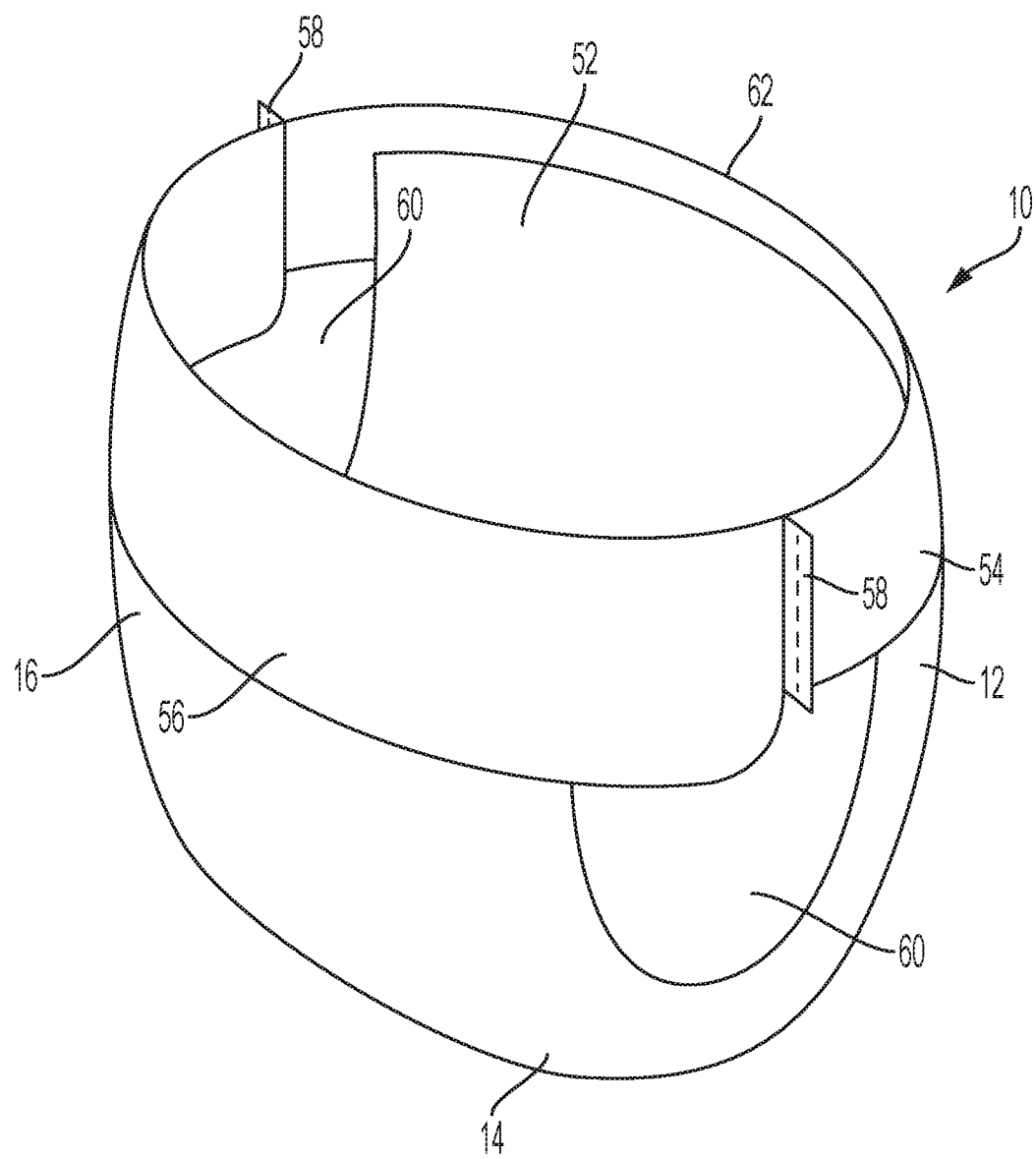
FIG. 5 is a rear perspective view of the absorbent article of FIG. 4.
Figure 6:
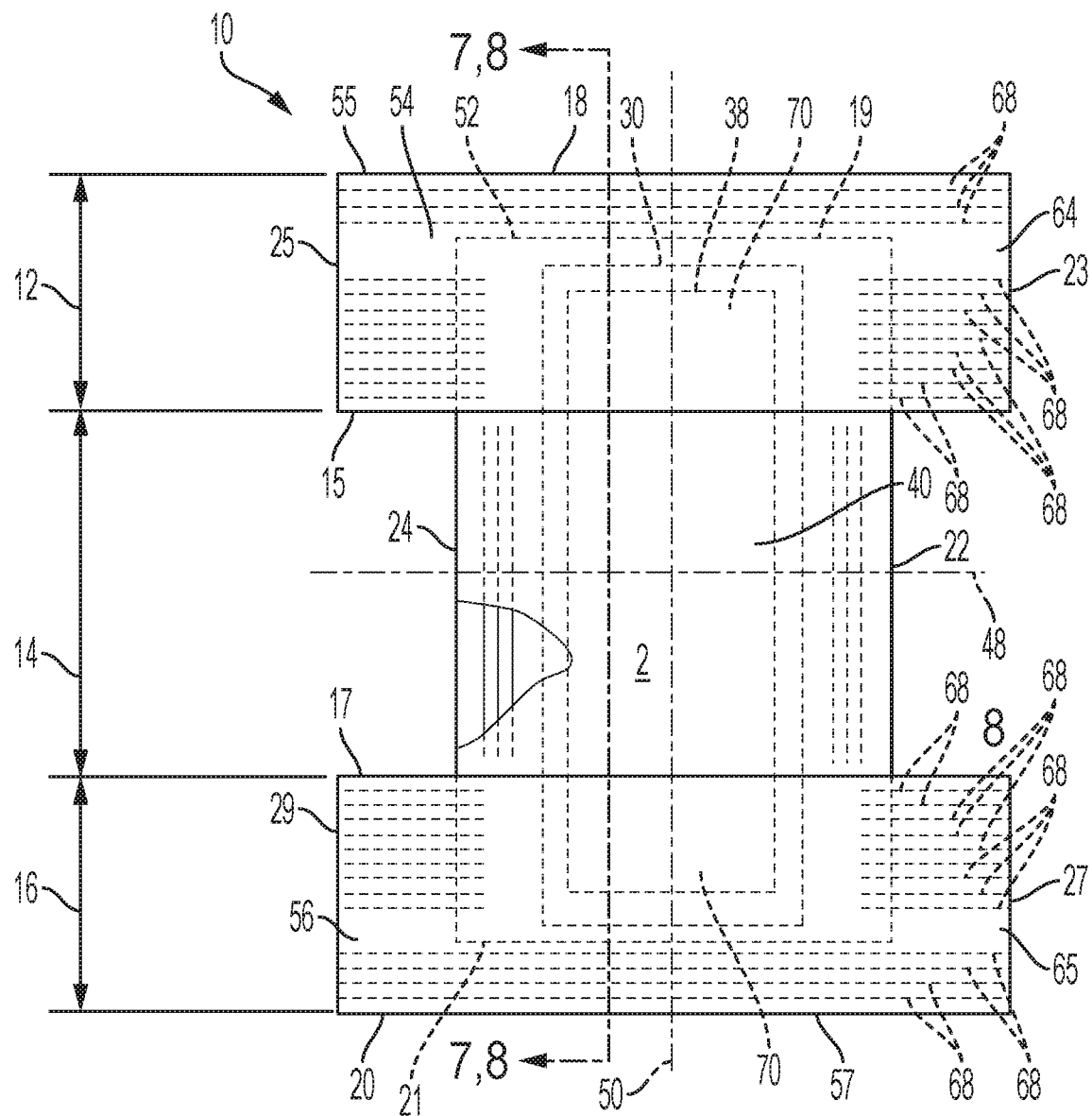
FIG. 6 is a plan view of the absorbent article of FIG. 4, laid flat, with a garment-facing surface facing the viewer.
Figure 7:
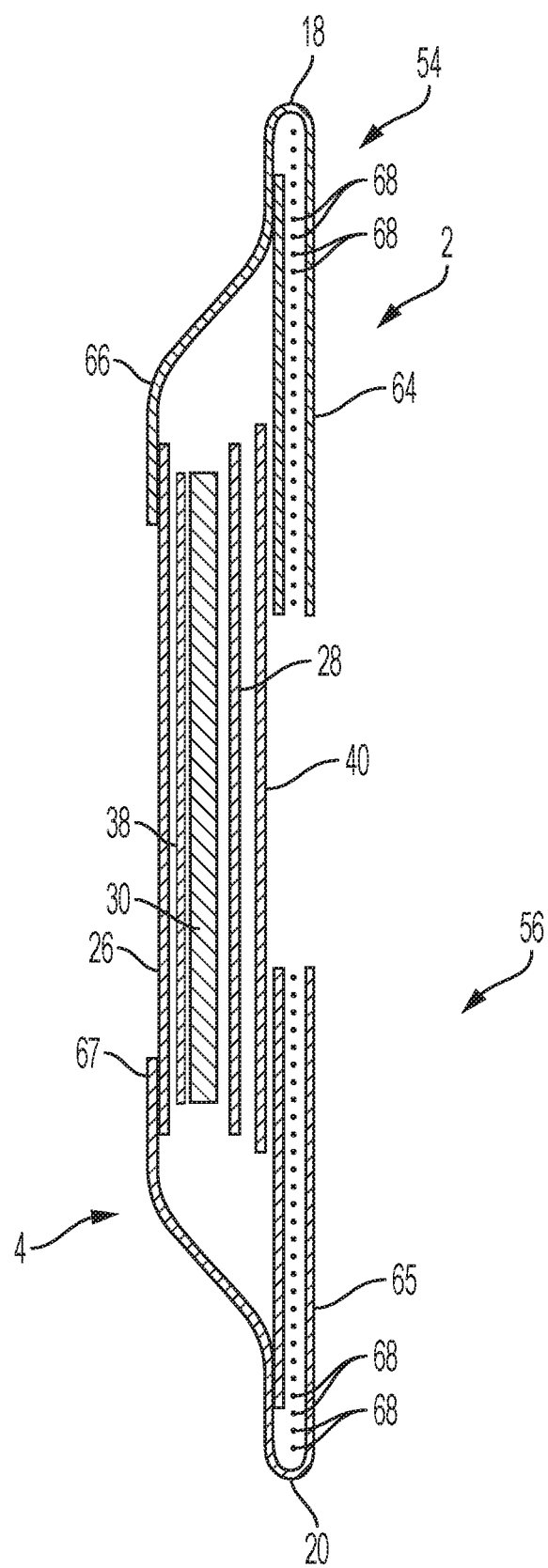
FIG. 7 is a cross-sectional view of the absorbent article taken about line 7-7 of FIG. 6.
Figure 8:
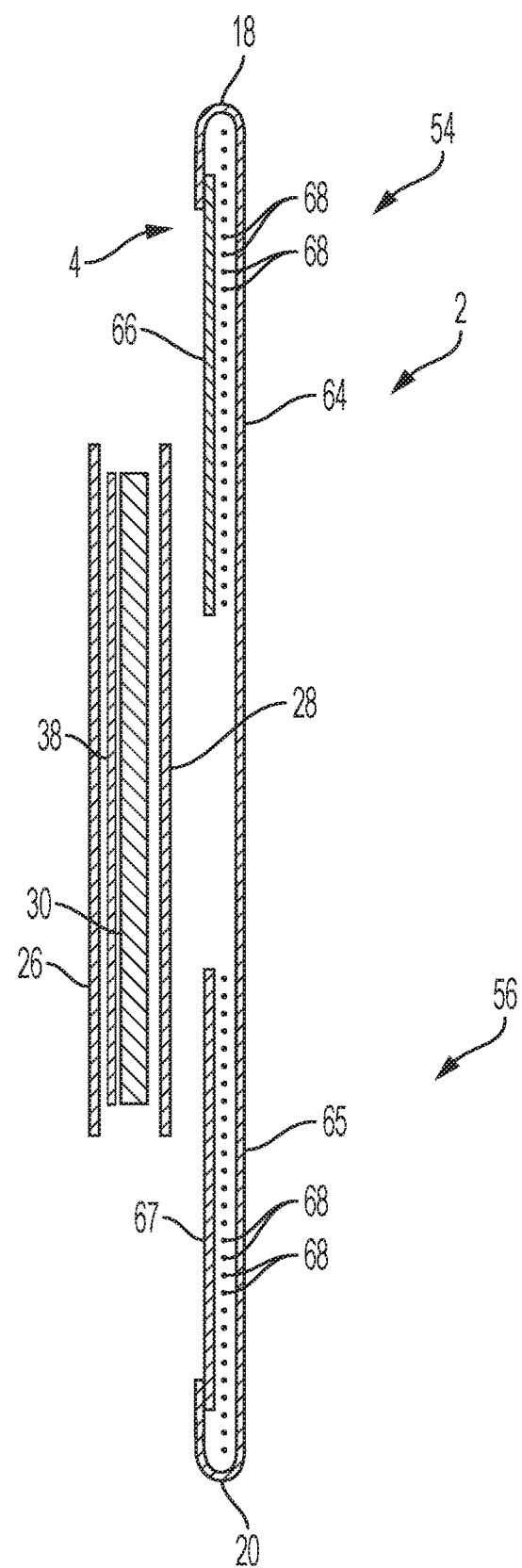
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 31), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet. The topsheet may comprise a bond pattern, apertures, and/or three-dimensional features.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features.

Absorbent Core

Figure 9:
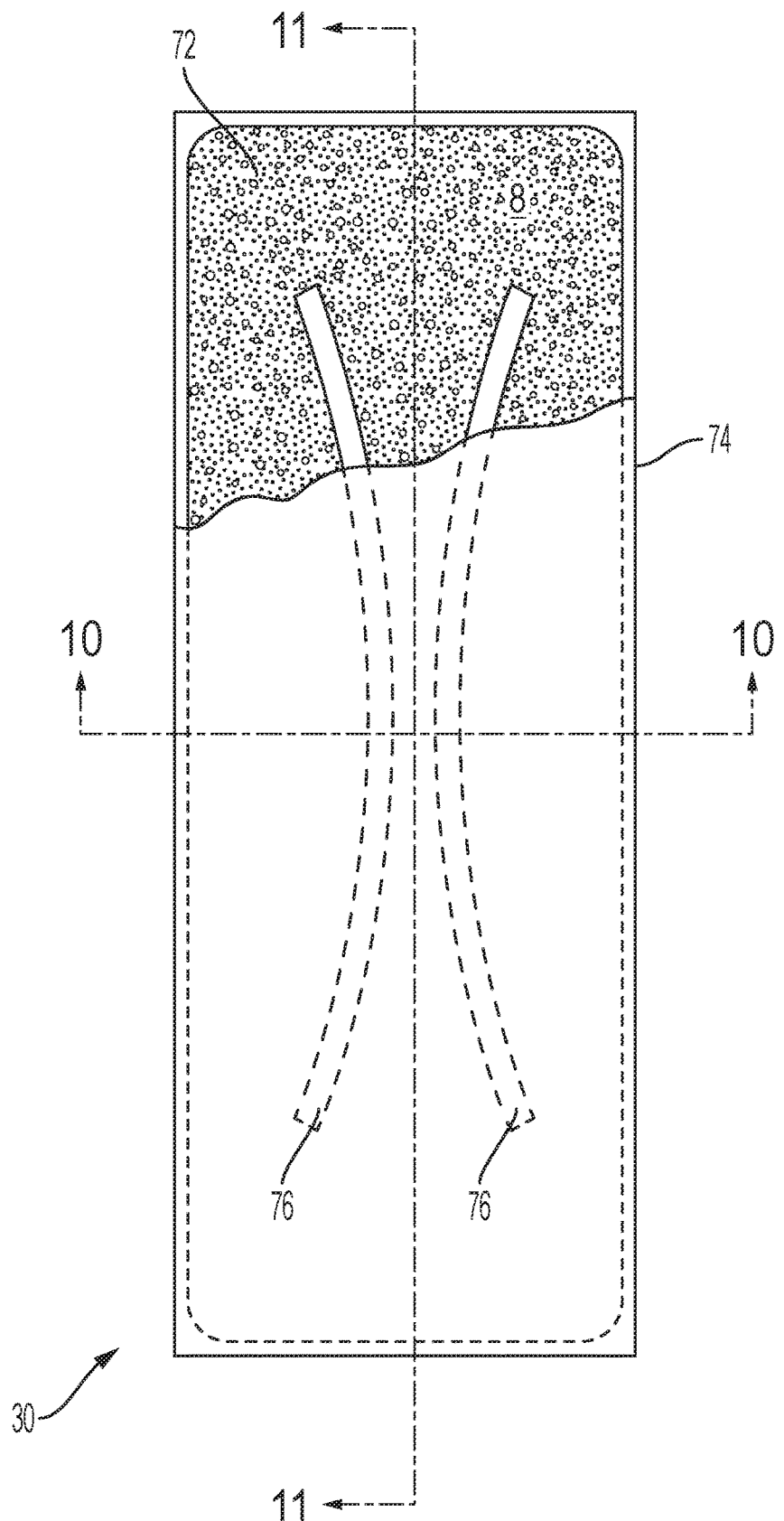
FIG. 9 is a plan view of an example absorbent core or an absorbent article.
Figure 10:
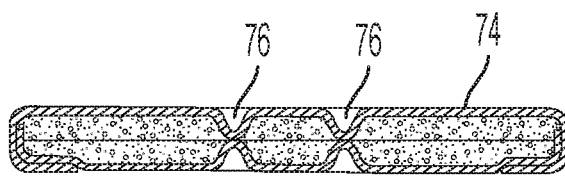
FIG. 10 is a cross-sectional view, taken about line 10-10, of the absorbent core of FIG. 9.
Figure 11:
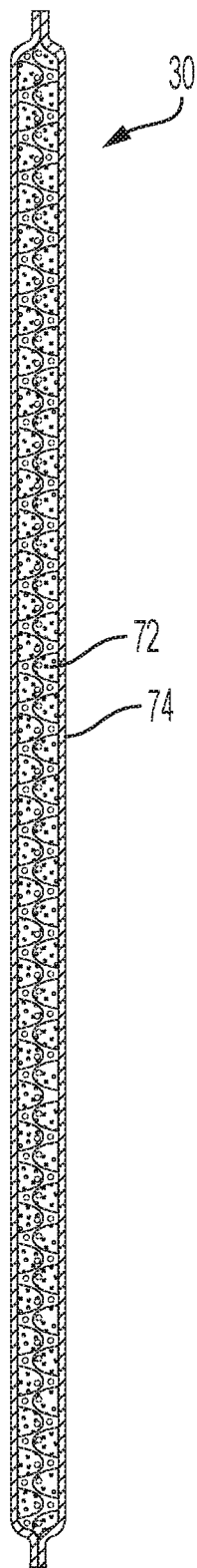
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material and may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14. The barrier leg cuffs may comprise a nonwoven material comprising a bond pattern and/or three-dimensional features.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article. The elastic waistband may comprise a nonwoven material comprising a bond pattern, apertures, and/or three-dimensional features.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa. The landing zone 44 may comprise a nonwoven material comprising a bond pattern, apertures, and/or three-dimensional features.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2. The ears may comprise one or more nonwoven materials comprising bond patterns, apertures, and/or three-dimensional features. The back and/or front ears may each comprise tapes comprising fasteners 46. The taps may comprise one or more nonwoven materials comprising bond patterns, apertures, and/or three-dimensional features.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages. The packages may have a bond pattern and/or three-dimensional features that match or are similar to bond patterns, apertures, and/or three-dimensional features on nonwoven materials of the absorbent articles within the packages.

Sanitary Napkin

Figure 12:
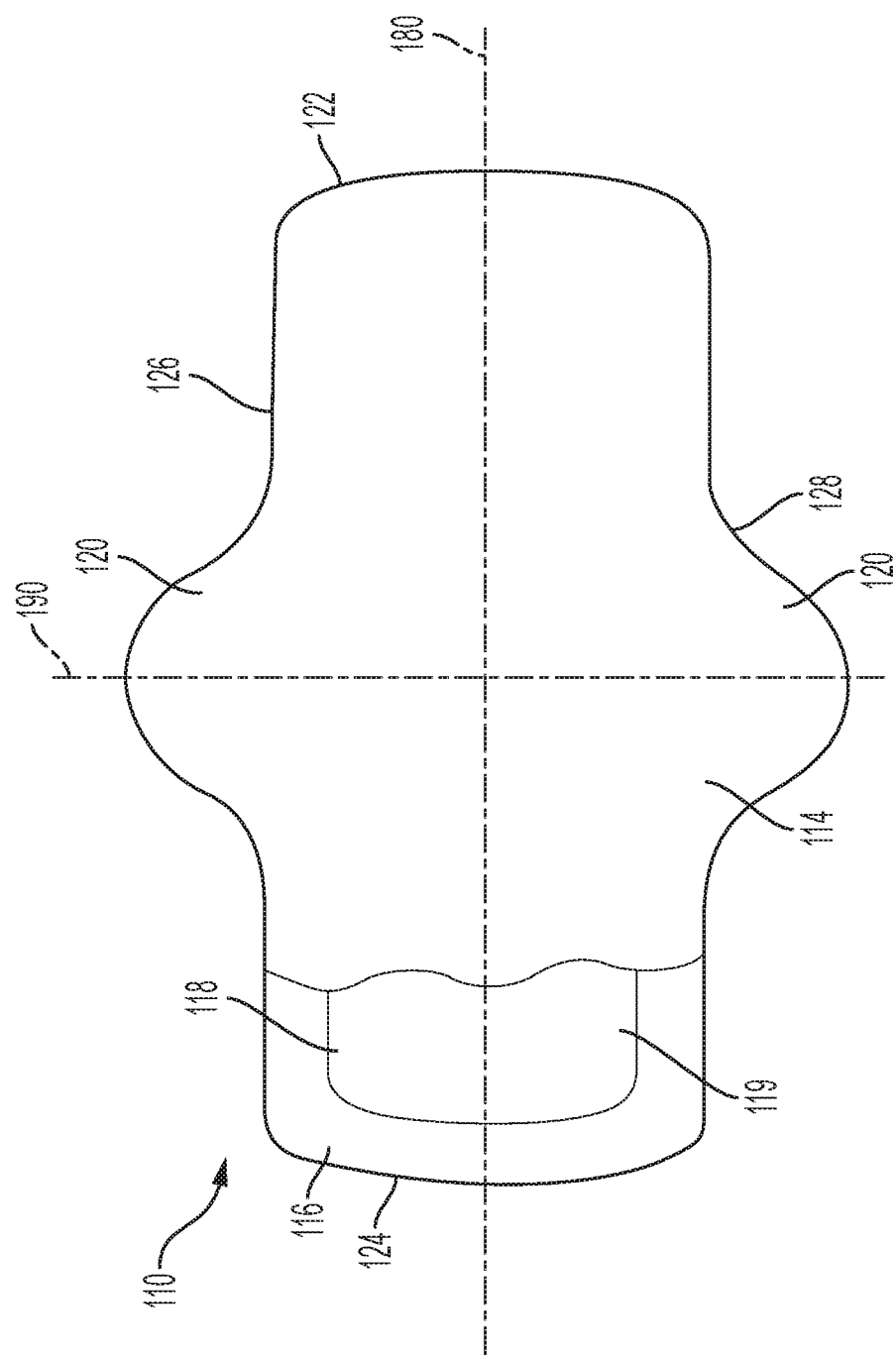
FIG. 12 is a plan view of an example absorbent article of the present disclosure that is a sanitary napkin.
Figure 13:
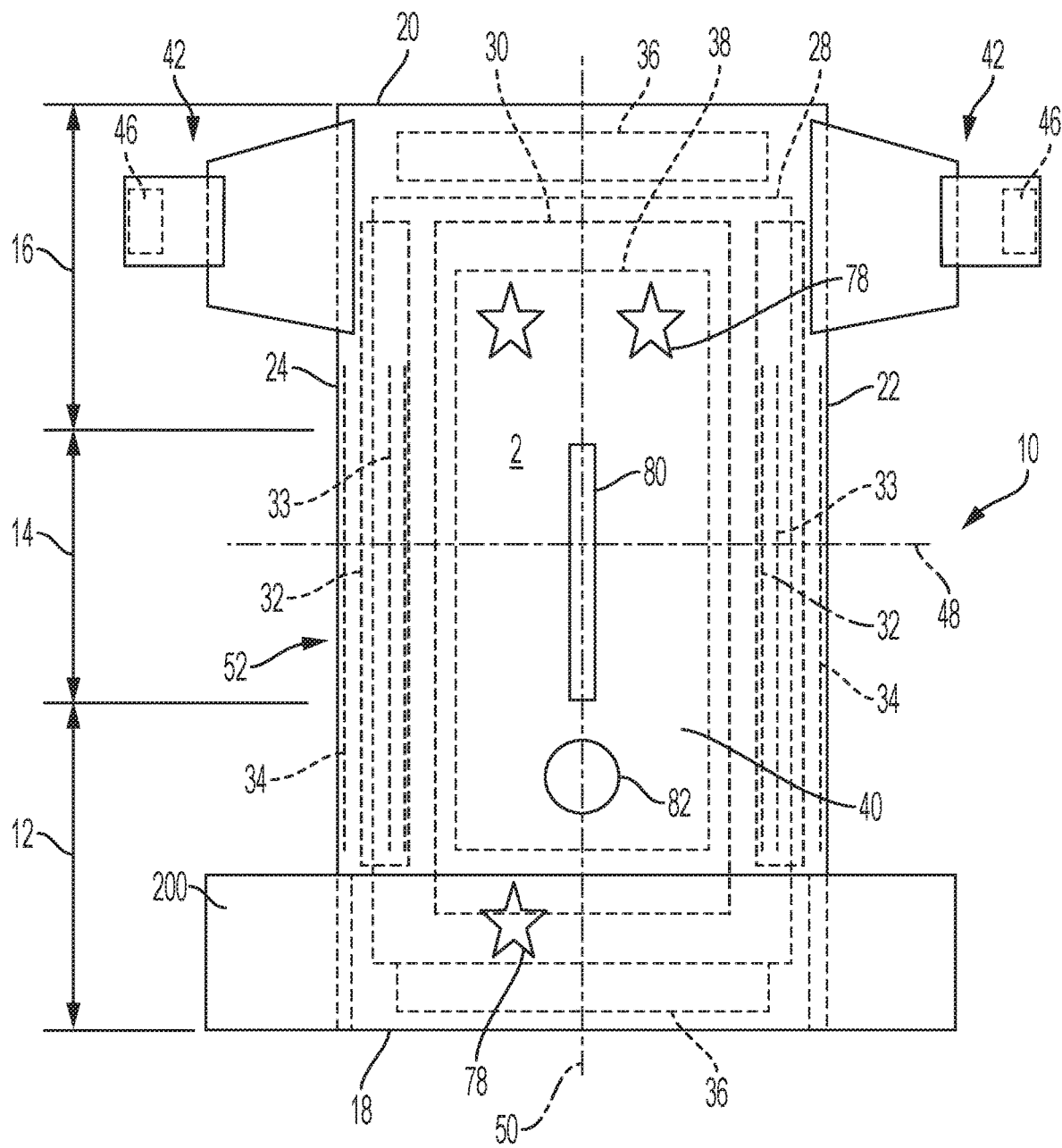
FIG. 13 is a plan view of an example absorbent article in the form of a taped diaper with a discrete, non-elasticized front belt, garment-facing surface facing the viewer, in a flat laid-out state.
Figure 14:
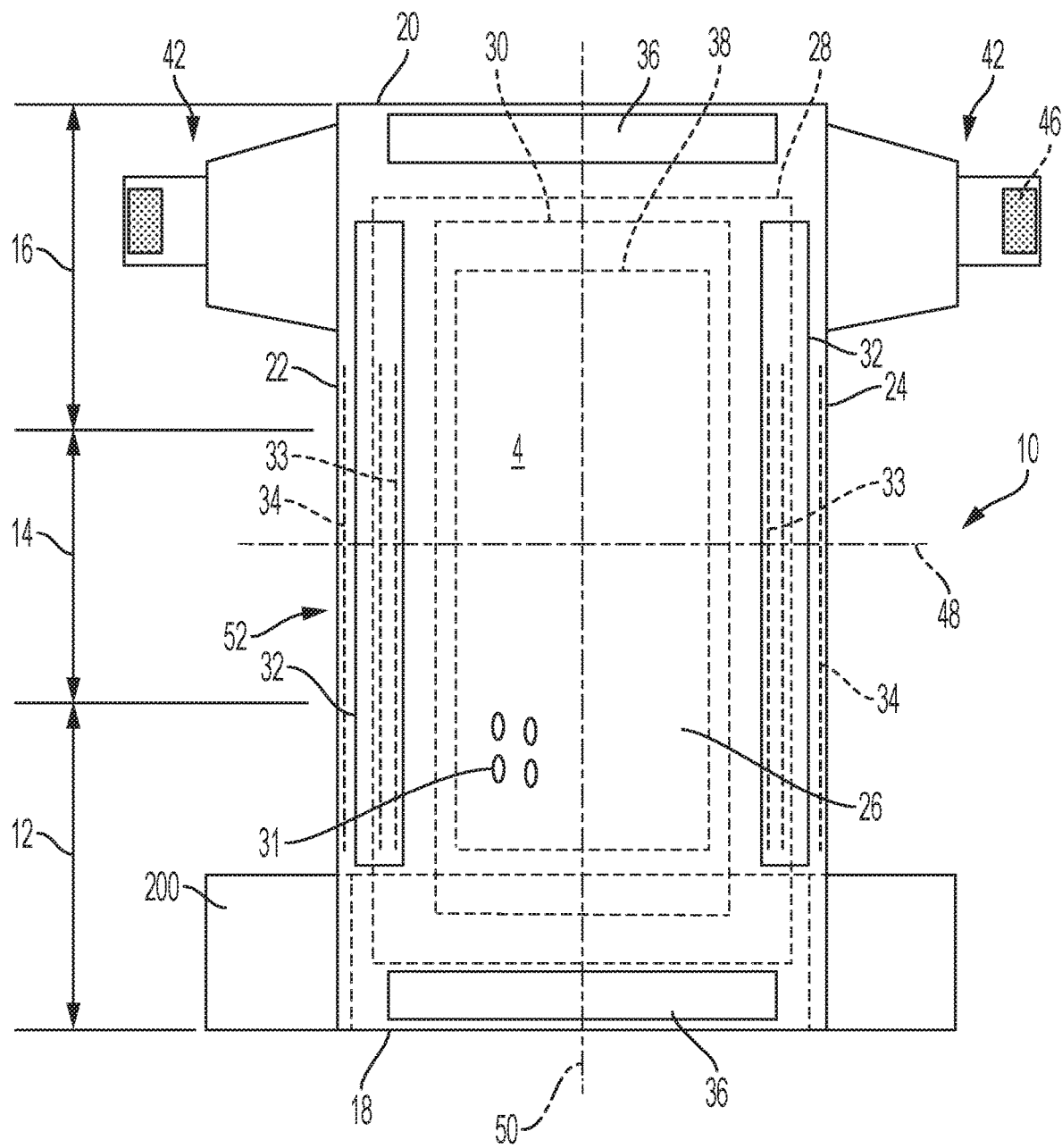
FIG. 14 is a plan view of the example absorbent article of FIG. 13 with a discrete, non-elasticized front belt, wearer-facing surface facing the viewer, in a flat laid-out state.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art. The sanitary napkin 110 may have a bond pattern, apertures, and/or three-dimensional features on two different nonwoven components or portions of the same nonwoven component (e.g., two different portions of the topsheet, or the topsheet and the wings).

Garment-Like Absorbent Articles

The garment-like absorbent articles of the present disclosure may have at least one or at least two different nonwoven absorbent article components that have patterns on portions of the garment-facing surface 2 and/or the wearer-facing surface 4. In some instance, one pattern may be on the garment-facing surface 2 and the other pattern may be on the wearer-facing surface, for example. The patterns may be formed by apertures, bonds, printing, and/or graphics. Bonds, as used herein, may comprise thermal bonds, ultrasonic bonds, pressure bonds, heat and pressure bonds, embossments, embossments that form three-dimensional features, and/or mechanical deformations that produce three-dimensional features, for example. The various nonwoven absorbent article components may be or comprise at least a portion of a topsheet, an ear, a leg cuff, an outer cover nonwoven material, a discrete landing zone, a discrete, non-elasticized front belt, a wing of a sanitary napkin, a belt of a pant, a waistband, or various other absorbent article components.

A first nonwoven component of an absorbent article may comprise a first pattern on a first portion of the garment-facing surface 2 and/or the wearer-facing surface 4. The first pattern may comprise a repeating pattern of apertures, bonds, printing, and/or graphics that may or may not form a plurality of first repeat units. A portion of, or all of, the first pattern within the first repeat units may be the same or substantially the same (e.g., process tolerances in forming the material). The first nonwoven component may have a first texture at least partially caused by the apertures and/or bonds, wherein the first texture may have an Sq value in the range of about 0.11 to about 0.4, according to the Surface Texture and Height Test herein. As an example, the first nonwoven component may comprise the outer cover nonwoven material 40 or at least a portion thereof. The first nonwoven component may also comprise any other suitable nonwoven component of an absorbent article, such as at least a portion of an ear, a belt, a waistband, a topsheet, and/or a wing of a sanitary napkin, for example. If printing is used, and the first component is an outer cover nonwoven material, the printing may occur on the backsheet film and be visible through the outer cover nonwoven material. In some instances, only a first nonwoven component with a repeating pattern of apertures, bonds, printing, and/or graphics may be provided on an absorbent article. Example components may be an outer cover nonwoven material or a topsheet.

A second nonwoven component of an absorbent article may comprise a second pattern on a first portion of the garment-facing surface 2 and/or the wearer-facing surface 4. The second pattern may comprise a repeating pattern of apertures, bonds, printing, and/or graphics that may or may not form a plurality of second repeat units. A portion of, or all of, the second pattern within the second repeat units may be the same or substantially the same (e.g., process tolerances in forming the material). The second nonwoven component may have a second texture at least partially caused by the apertures and/or bonds, wherein the second texture has an Sq value in the range of about 0.11 to about 0.4, according to the Surface Texture and Height Test herein. As an example, the second nonwoven component may comprise a discrete landing zone or a discrete, non-elasticized (or elasticized) front belt or at least a portion of the same. The second nonwoven component may also comprise any other suitable nonwoven component of an absorbent article, such as at least a portion of an ear, a belt, a waistband, a topsheet, and/or a wing of a sanitary napkin, for example.

An example discrete landing zone 44 is illustrated in FIG. 1. By discrete landing zone, it is meant that the landing zone is a separate component from the outer cover nonwoven material and not just a portion of the outer cover nonwoven material. The discrete landing zone may be one piece or may be multiple pieces, as illustrated in FIG. 1 with dashed lines. If two pieces are desired, a first piece 44' may be spaced a distance from a second piece 44" such that the first piece 44' does not overlap or contact the second piece 44". The discrete landing zone, whether one or two pieces, may be attached to a garment-facing surface 2 of the absorbent article.

An example of a discrete, non-elasticized front belt 200 is illustrated in FIGS. 13-16. In some instances, the front belt 200 may be elasticized or partially elasticized. The discrete, non-elasticized front belt 200 may be a separate material attached to the garment-facing surface 2 and/or the wearer-facing surface 4 of the absorbent article 10.

In an instance, a first portion of the outer cover nonwoven material may have the first pattern and a second portion of the outer cover nonwoven material may have the second pattern. In such an instance, the second portion may act as a landing zone.

Figure 15:
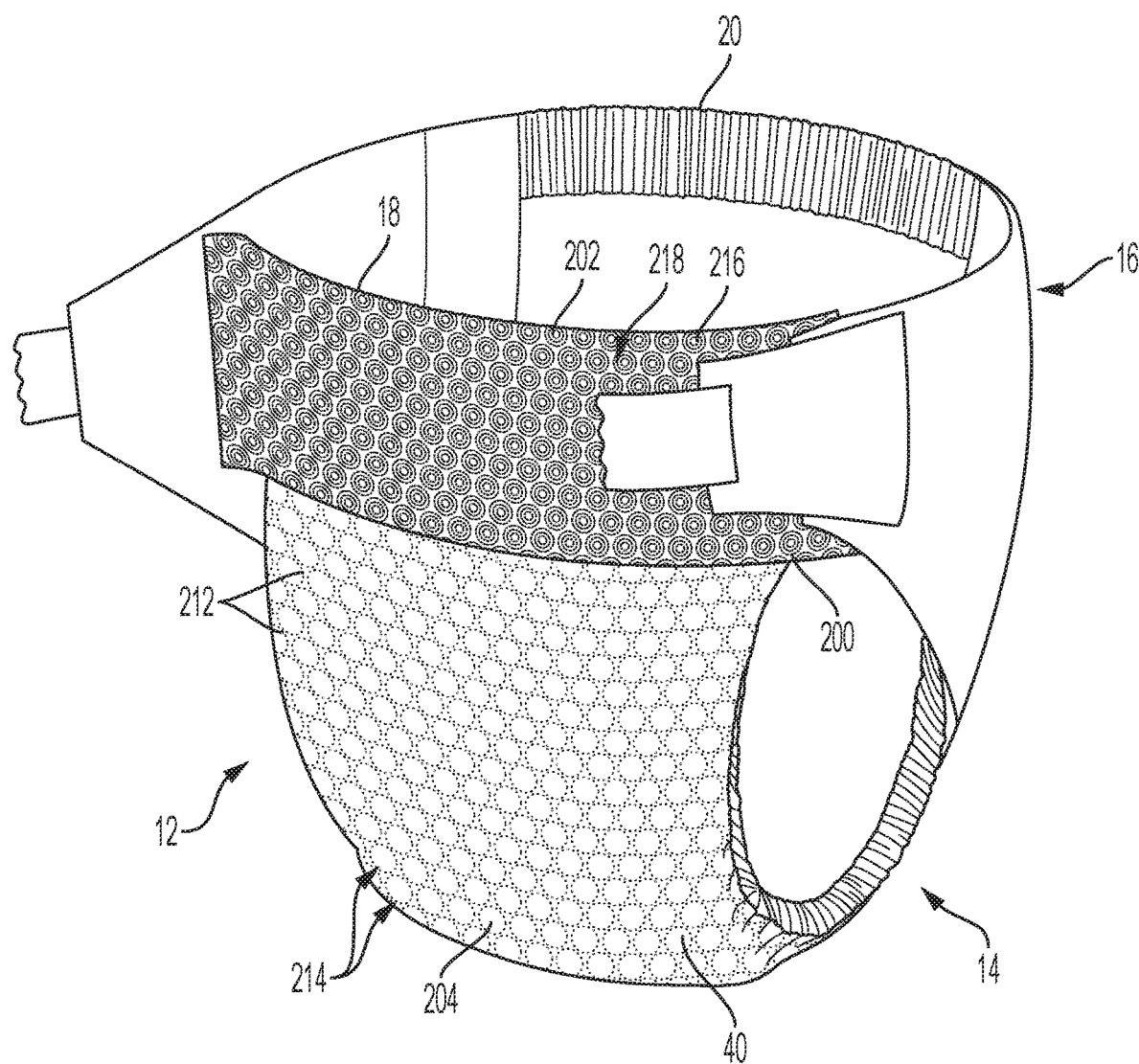
FIG. 15 is a front perspective view of the absorbent article of FIGS. 13 and 14 with a discrete, non-elasticized front belt in a partially fastened position and having first and second patterns on two different components.

Referring to FIG. 15, the outer cover nonwoven material 40 (e.g., first component) may have a first repeating pattern 204 of apertures and/or bonds 212. The first repeating pattern 204 may have a plurality of first repeat units 214. A portion of the first repeating pattern 204 within at least a majority of the first repeat units 214 may be the same or substantially the same (e.g., process tolerances). The outer cover nonwoven material 40 may have a first texture Sq value in the range of about 0.11 mm to about 0.4 mm, or about 0.11 mm to about 0.35 mm, specifically reciting all 0.0001 mm increments within the specified ranges and all ranges formed therein or thereby, according to the Surface Texture and Height Test herein.

The discrete, non-elasticized front belt 200, or discrete landing zone, (e.g., second component) may have a second repeating pattern 202 of apertures and/or bonds 216. The second repeating pattern 202 may have a plurality of second repeat units 218. A portion of the second repeating pattern 202 within at least a majority of the second repeat units 218 may be the same or substantially the same (e.g., process tolerances). The discrete, non-elasticized front belt 200, or the discrete landing zone may have a second texture Sq value in the range of about 0.1 mm to about 0.15 mm, specifically reciting all 0.0001 mm increments within the specified ranges and all ranges formed therein or thereby, according to the Surface Texture and Height Test herein.

The first texture of the first pattern 204 and the second texture of the second pattern 202 may be the same or different. At least some of, or all of, the first repeat units 214 comprising the portion of the first pattern 204 may comprise a first shape or first design. At least some of, or all of, the second repeat units 218 comprising the portion of the second pattern 202 may comprise a second shape or second design. The first shape or design may be the same as or substantially similar to the second shape or design. Substantially similar may mean generally the same pattern or design but with slightly different sizes, scales, and/or shapes, for example. For example, the first repeat units 214 may comprise circles and the second repeat units 218 may comprise circles, as illustrated in FIG. 15. As another example, the first repeat units 214 may comprise triangles, wavy lines, squares, ovals, clouds, hearts, and/or other shapes or patterns and the second repeat units may also comprise triangles, wavy lines, squares, ovals, clouds, hearts, and/or other shapes or patterns. Even though the first and second repeat units may comprise similar shapes or designs, the size of the shapes or designs may very between the first and second repeat units. Also, the density and/or size of the apertures and/or bonds in the various repeat units may differ. Likewise, in some instances, the first pattern 204 may be different than the second pattern 202, although such patterns may correspond or be substantially similar to create a garment-like impression in the absorbent article.

Even though the at least two nonwoven components of an absorbent article are described herein as being complimentary to each other, they may also be used separate from one another. For example, an outer cover nonwoven material having the texture and repeat units discussed herein may be used in an absorbent article separate from the discrete landing zone or discrete, non-elasticized front belt having the texture and repeat units. The same applies to the discrete landing zone or discrete, non-elasticized front belt without the outer cover nonwoven material.

Figure 16:
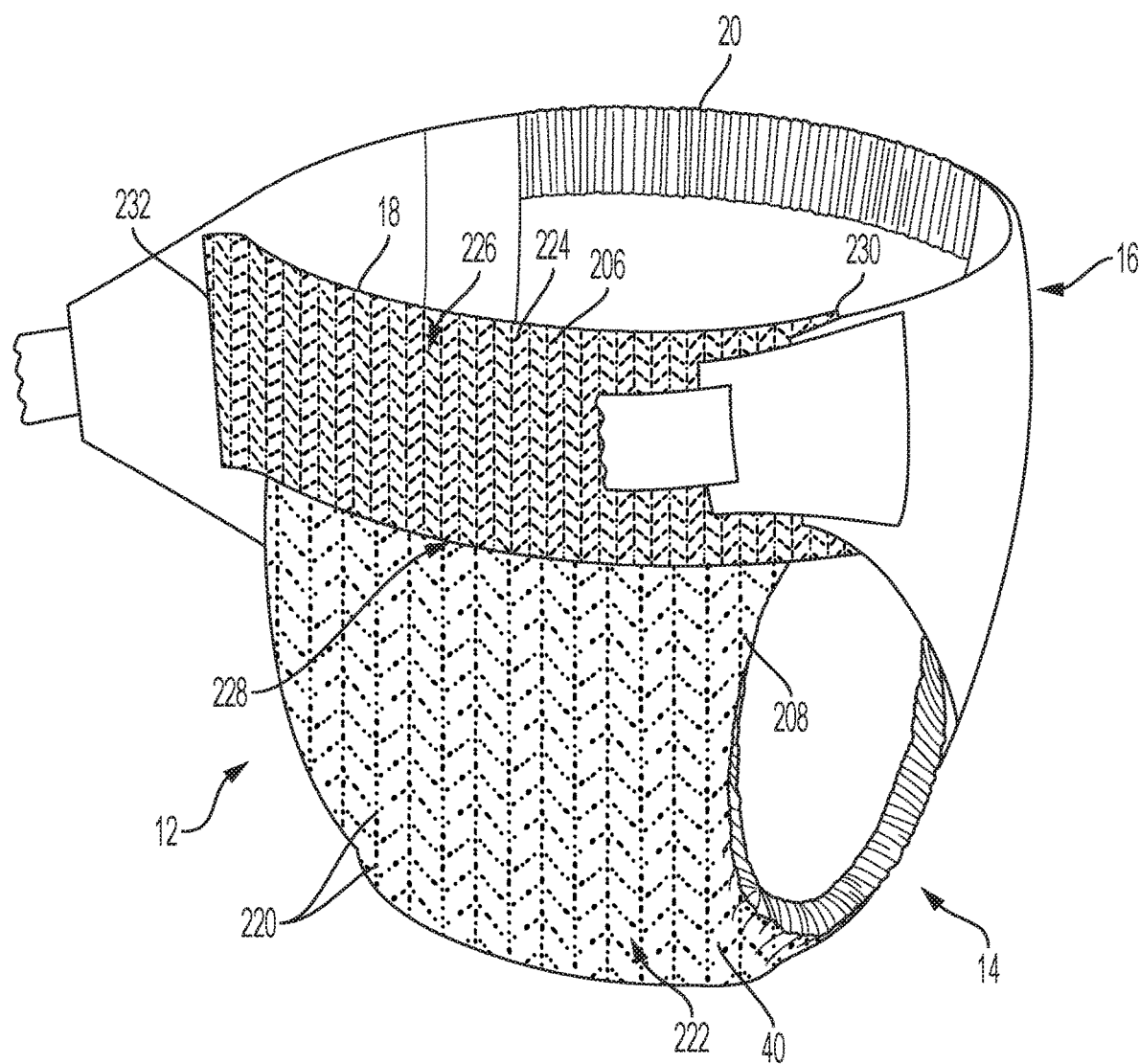
FIG. 16 is a front perspective view of the absorbent article of FIGS. 13 and 14 with a discrete, non-elasticized front belt in a partially fastened position and having third and fourth patterns on two different components.

Referring to FIG. 16, the outer cover nonwoven material 40 (e.g., first component) may comprise a first repeating pattern 208 of apertures and/or bonds 220. The first repeating pattern 208 may have a plurality of first repeat units 222. A portion of the first repeating pattern 206 within at least a majority of the first repeat units 222 may be the same or substantially the same (e.g., process tolerances). The first repeating pattern 208 may form a herringbone pattern. The outer cover nonwoven material 40 may have a first texture Sq value in the range of about 0.11 mm to about 0.4 mm, or about 0.11 mm to about 0.35 mm, specifically reciting all 0.0001 mm increments within the specified ranges and all ranges formed therein or thereby, according to the Surface Texture and Height Test herein.

The discrete, non-elasticized front belt 200, or discrete landing zone, (e.g., second component) may have a second repeating pattern 206 of apertures and/or bonds 224. The second repeating pattern 206 may have a plurality of second repeat units 226. A portion of the second repeating pattern 206 within at least a majority of the second repeat units 226 may be the same or substantially the same (e.g., process tolerances). The second repeating pattern 206 may form a herringbone pattern. The discrete, non-elasticized front belt 200, or discrete landing zone may have a second texture Sq value in the range of about 0.1 to about 0.15, specifically reciting all 0.0001 mm increments within the specified ranges and all ranges formed therein or thereby, according to the Surface Texture and Height Test herein.

Figure 17:
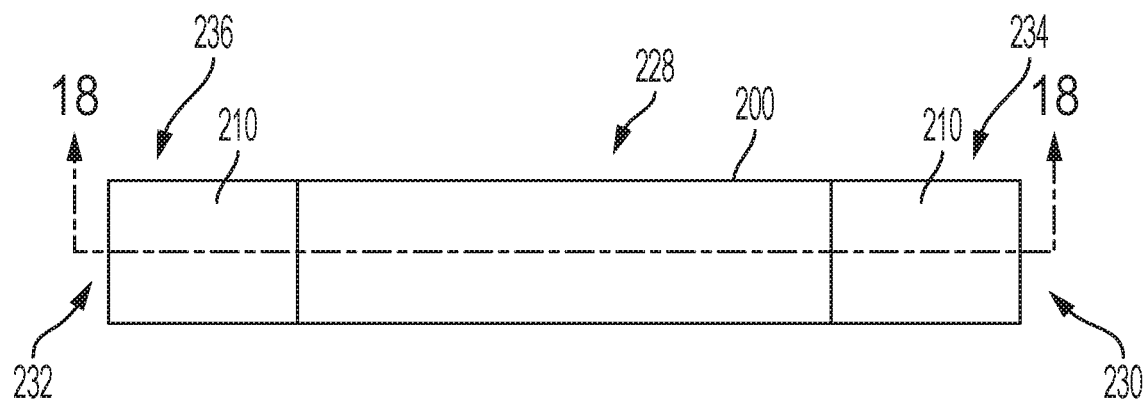
FIG. 17 is a plan view of a discrete, non-elasticized front belt having a first and second support members proximate to first and second ends thereof.
Figure 18:
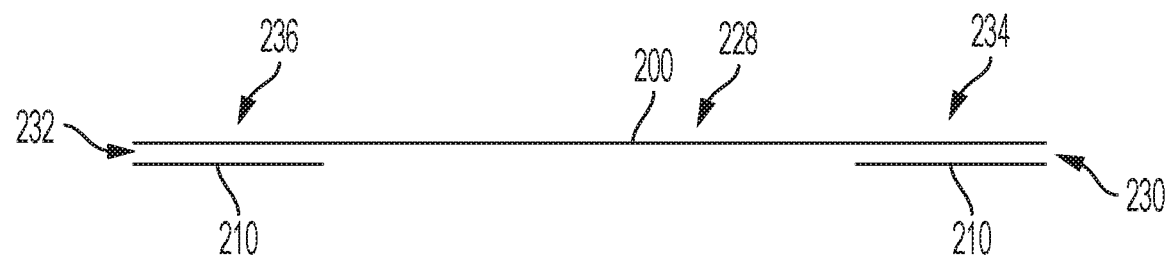
FIG. 18 is a cross-sectional view of the discrete, non-elasticized front belt, taken about line 18-18 of FIG. 17.
Figure 19:
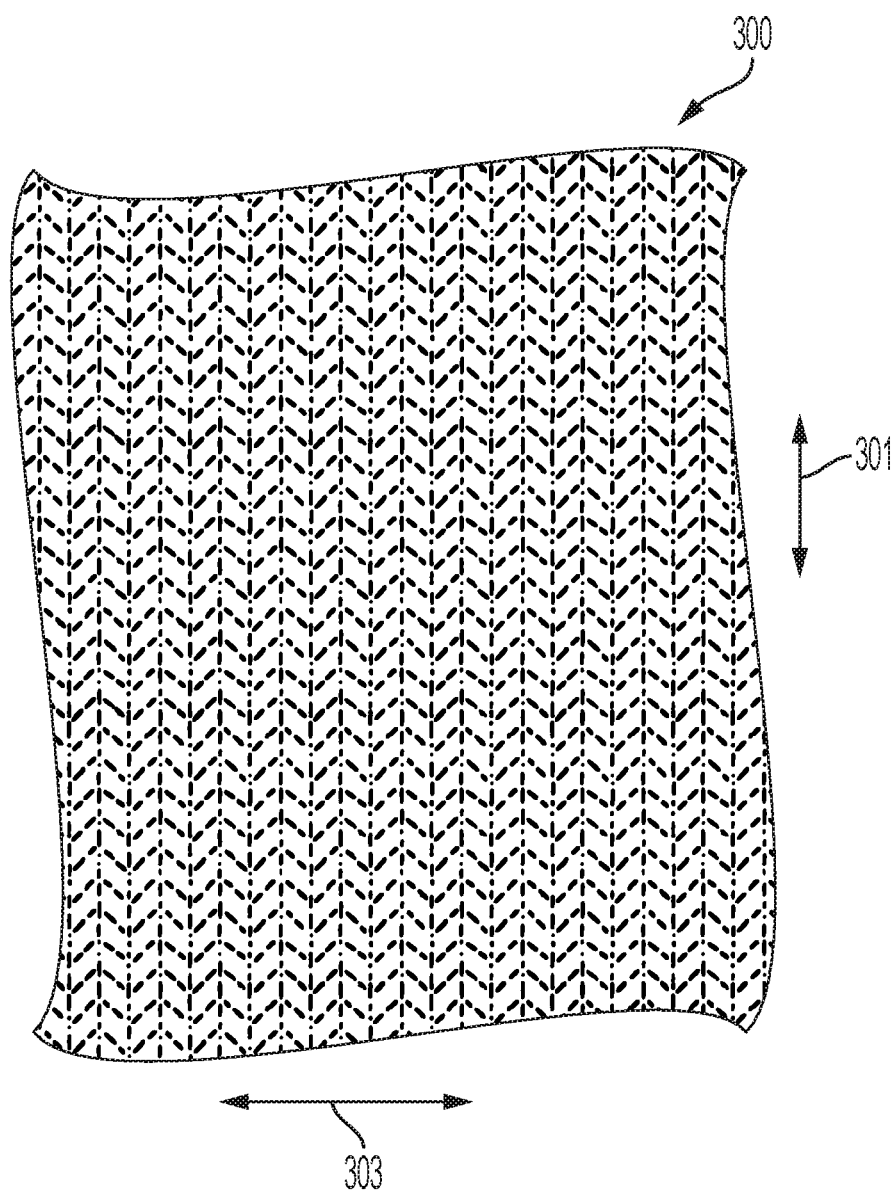
FIGS. 19-26 are example patterns for components of absorbent articles, such as an outer cover nonwoven materials, discrete landing zones, or discrete, non-elasticized front belts.

Referring to FIGS. 16-18, the discrete, non-elasticized front belt 200 may have a middle portion 228 that overlaps the outer cover nonwoven material. The front belt 200 may comprise a first lateral end 230 and a second, opposing lateral end 232. A first portion 234 of the front belt 200 may be positioned intermediate the first lateral end 230 and a first lateral edge of the outer cover nonwoven material. A second portion 236 of the front belt 200 may be positioned intermediate the second lateral end 232 and a second, opposing lateral edge of the outer cover nonwoven material. These first and second portions 234, 236 are free of overlap with the outer cover nonwoven material and, therefore, may be flimsy and not appear of high quality. To solve this issue, a support member 210 may overlap and be joined to the first and second portions 234, 236 to provide structural support to the first and second portions 234, 236. The support members may be a nonwoven material, a foam, a felt, a film, a cellulosic material or other suitable material that for providing support to the first and second portions 234, 236 of the front belt 200 that are free of overlap with the outer cover nonwoven material.

Figure 20:
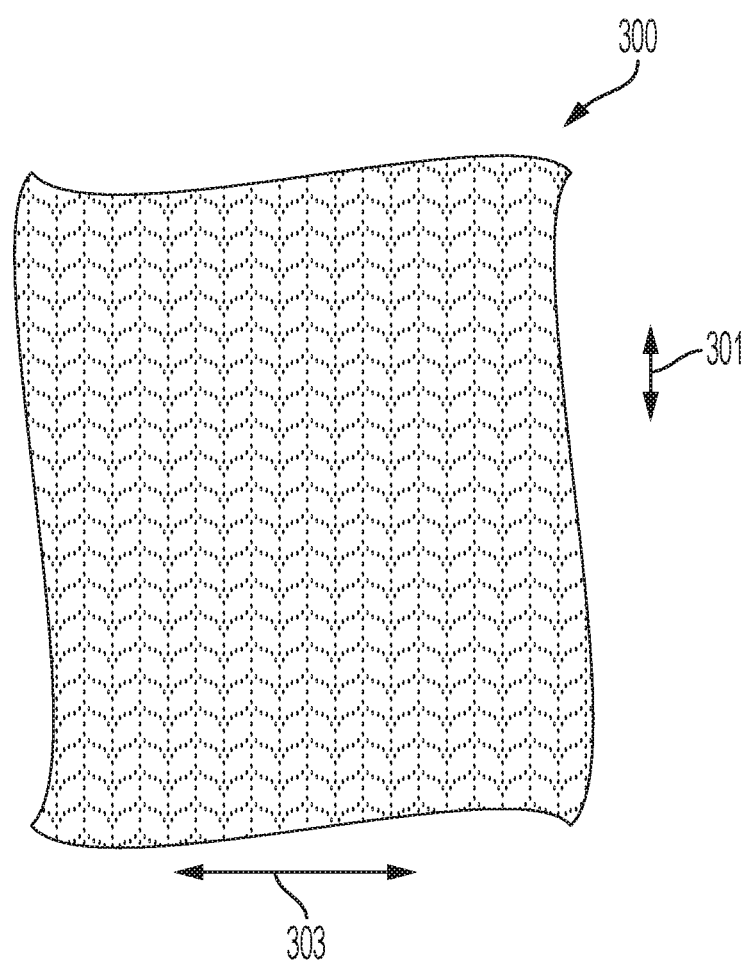
Figure 21:
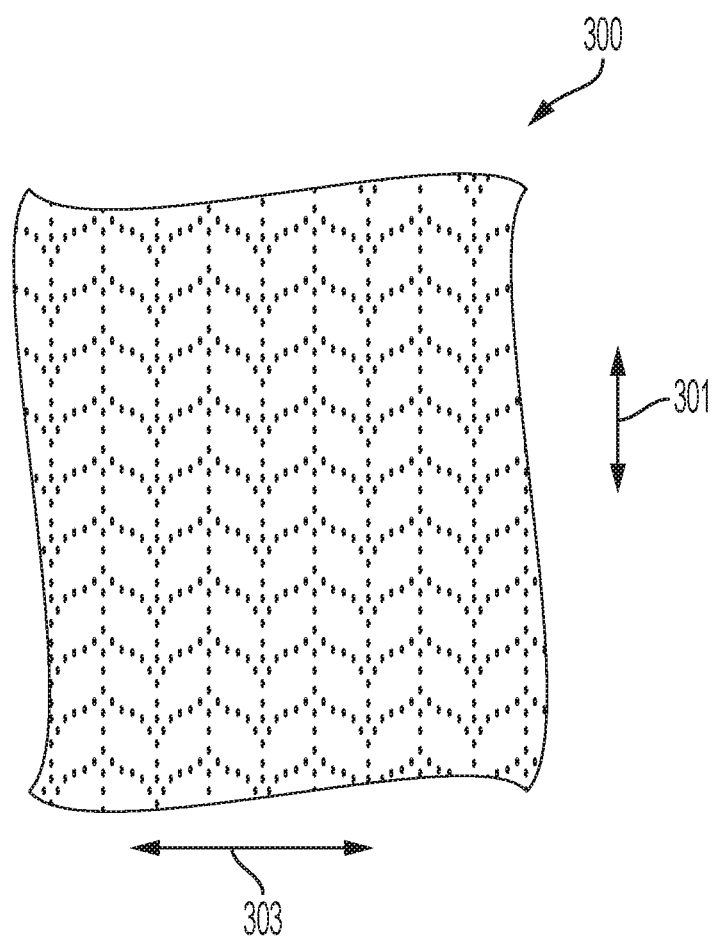
Figure 22:
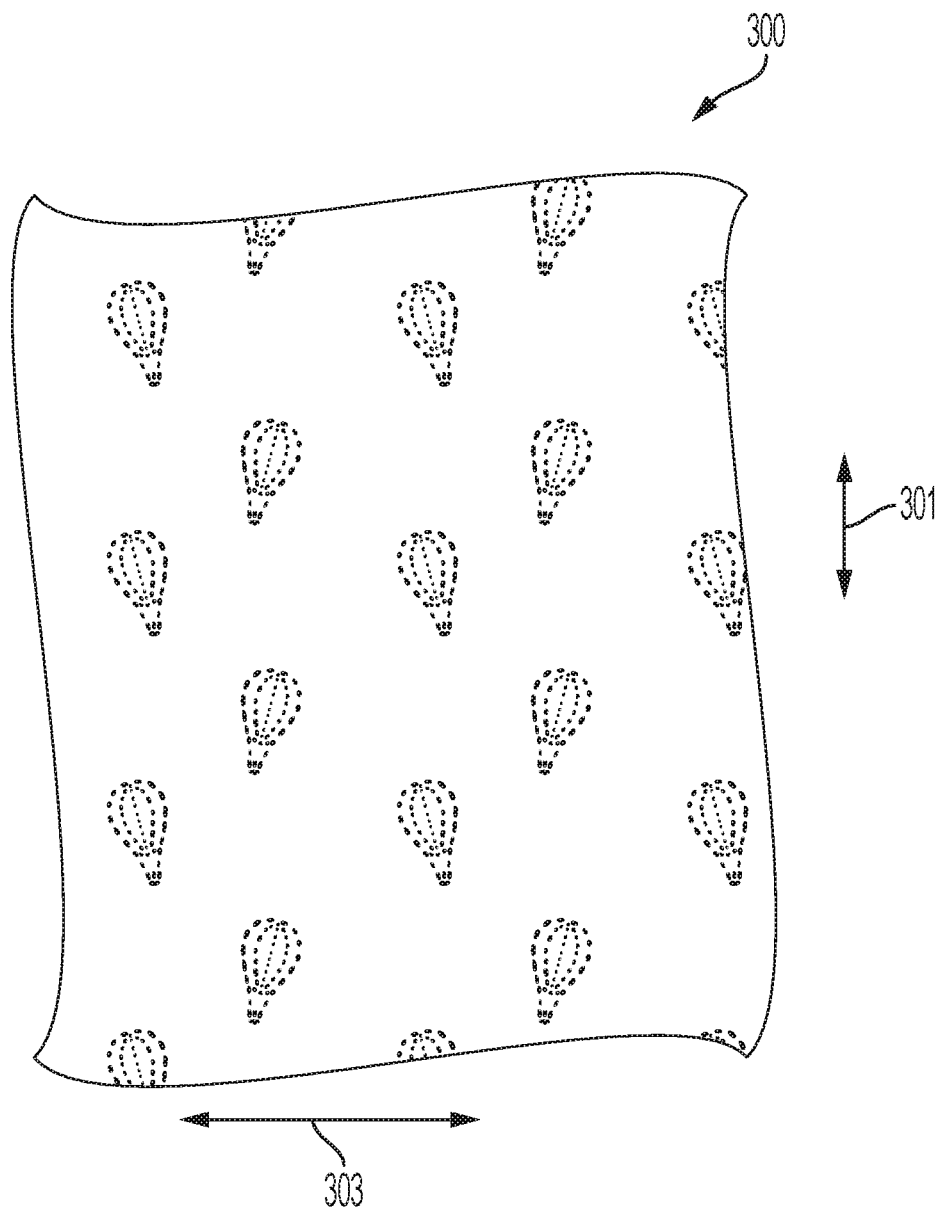
Figure 23:
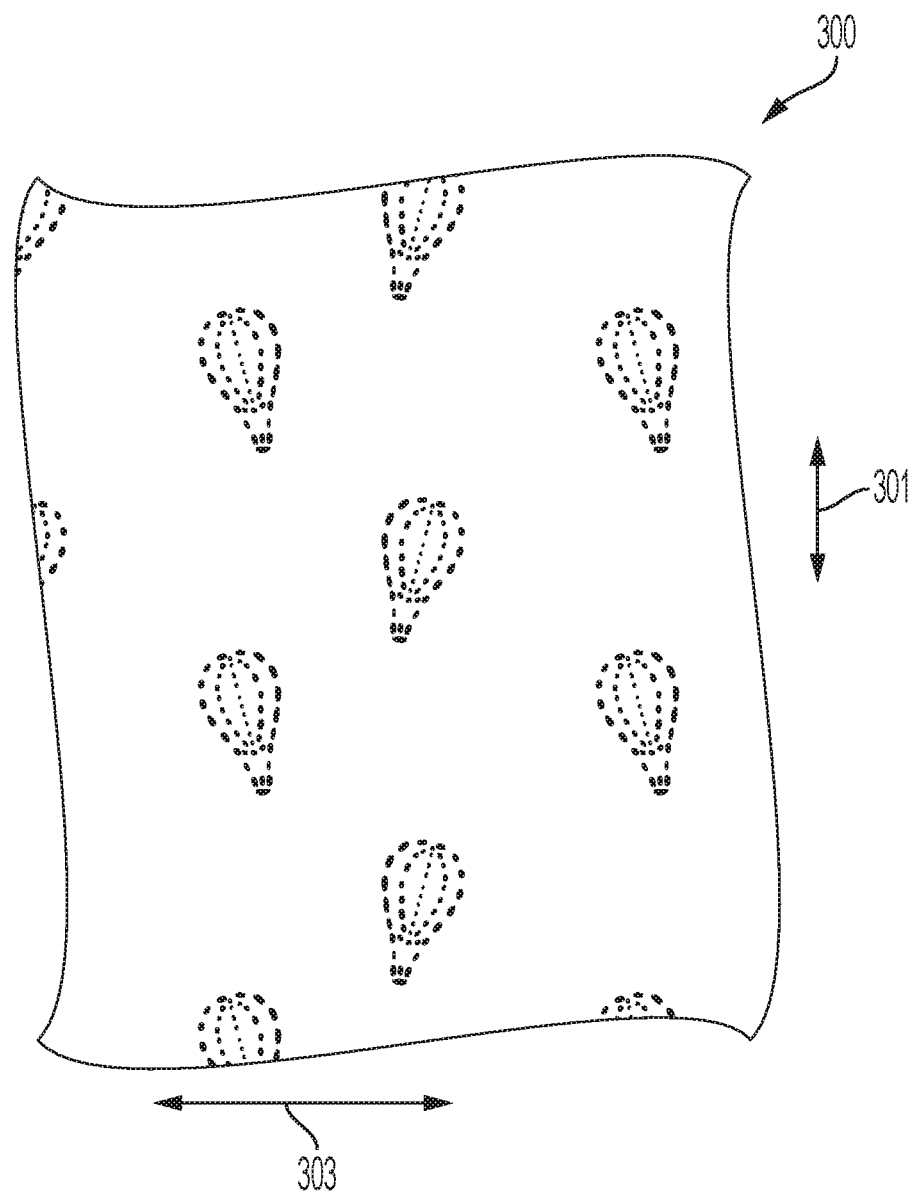
Figure 24:
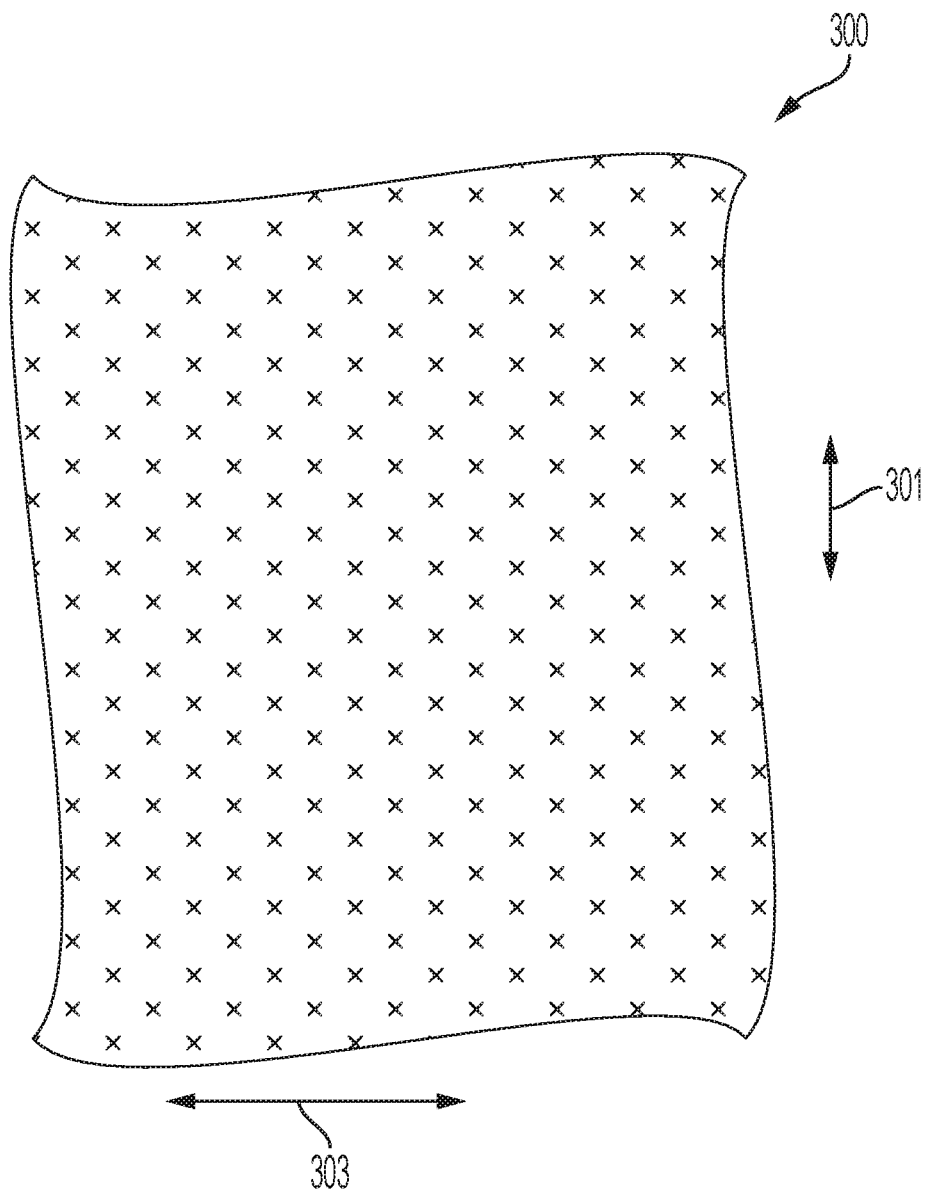
Figure 25:
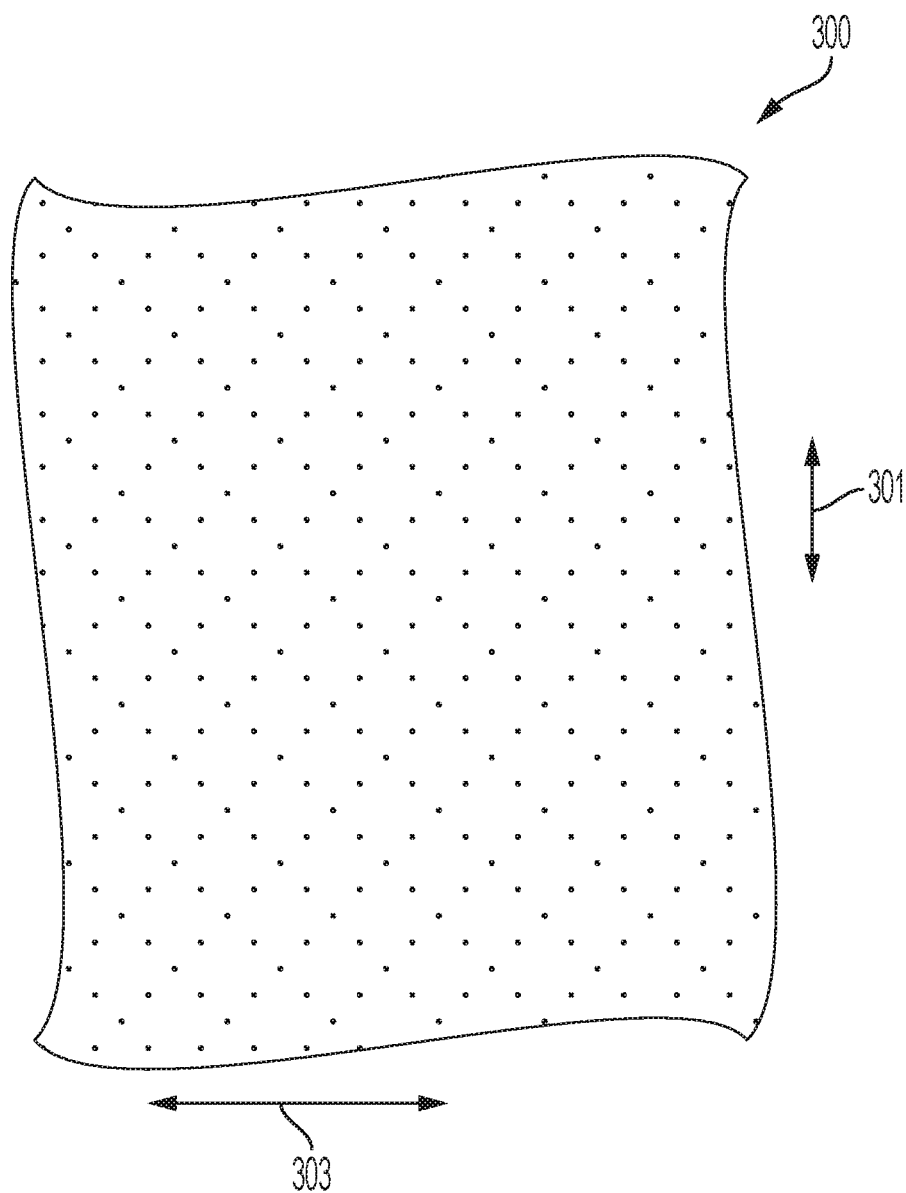
Figure 26:
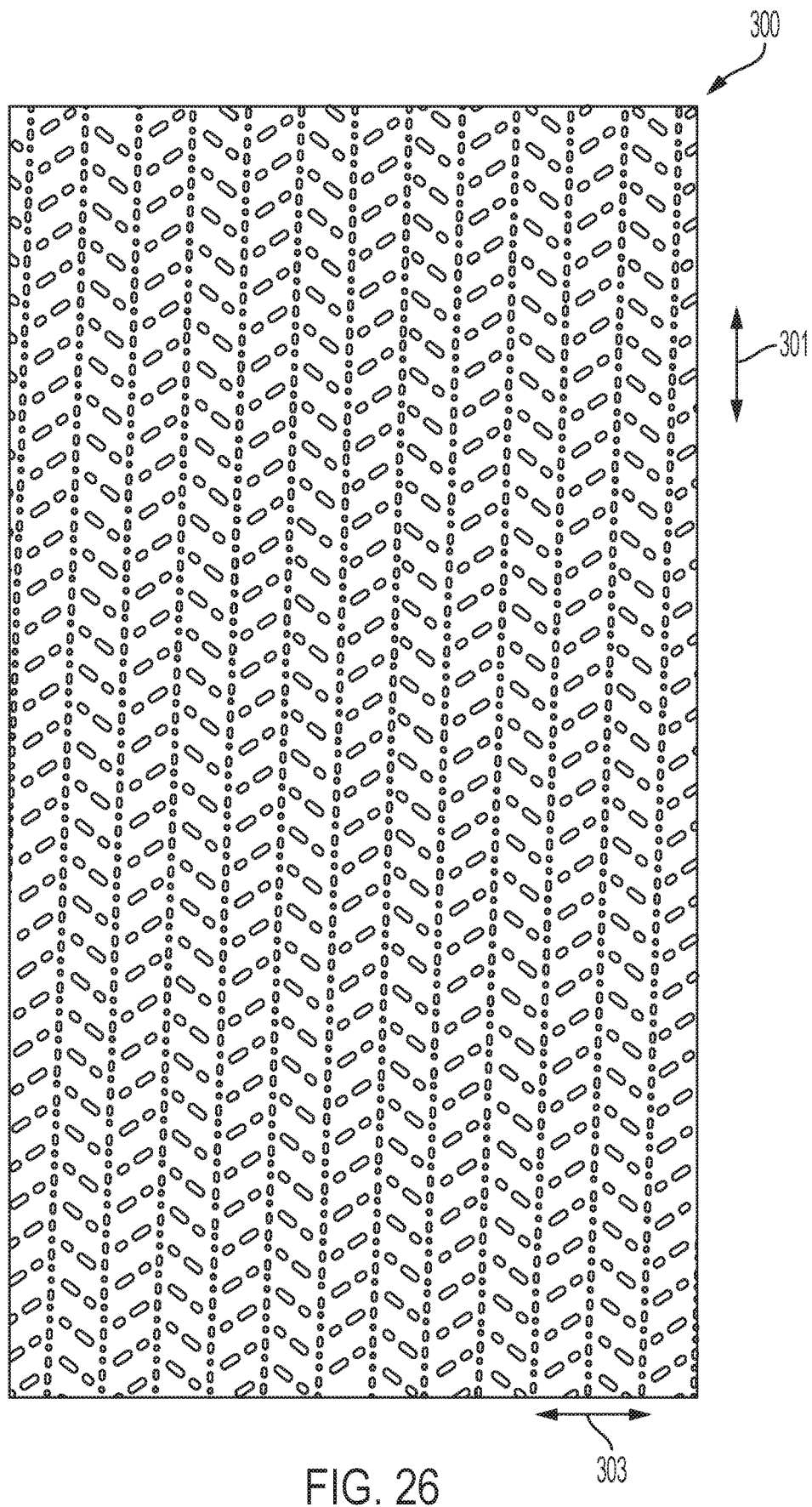

FIGS. 19-26 are example patterns 300 for components of absorbent articles, such as an outer cover nonwoven materials, discrete landing zones, or discrete, non-elasticized front belts. The pattern 300 of FIG. 19 may be used with one or more of the first and second patterns 208 and 206 of FIG. 16. FIGS. 20 and 21 may be used on two different nonwoven absorbent article components, such as an outer cover nonwoven material and a discrete landing zone or discrete, non-elasticized front belt. FIGS. 22 and 23 may be used on two different nonwoven absorbent article components, such as an outer cover nonwoven material and a discrete landing zone or discrete, non-elasticized front belt. FIG. 26 is a pattern 300 similar to the pattern of FIG. 19, but with adjacent rows within the pattern being "offset" from each other. In an embossing context, this helps in balancing the roll.

In FIGS. 19-26, axis 301 may or may not be generally parallel to the central longitudinal axis 50 (see FIG. 1) and axis 303 may or may not be generally parallel to the central lateral axis 48 (see FIG. 1). In some instances, axis 301 may be angled with respect to the central longitudinal axis 50, such as angled in the range of about 0.5 degrees to about 20 degrees, or about 1 degree to about 15 degrees, for example. This angling may reduce wear on bonding rolls comprising the discontinuous bond or aperture pattern.

FIGS. 19-21 and 26-28 illustrate versions of a herringbone pattern.

Figure 27:
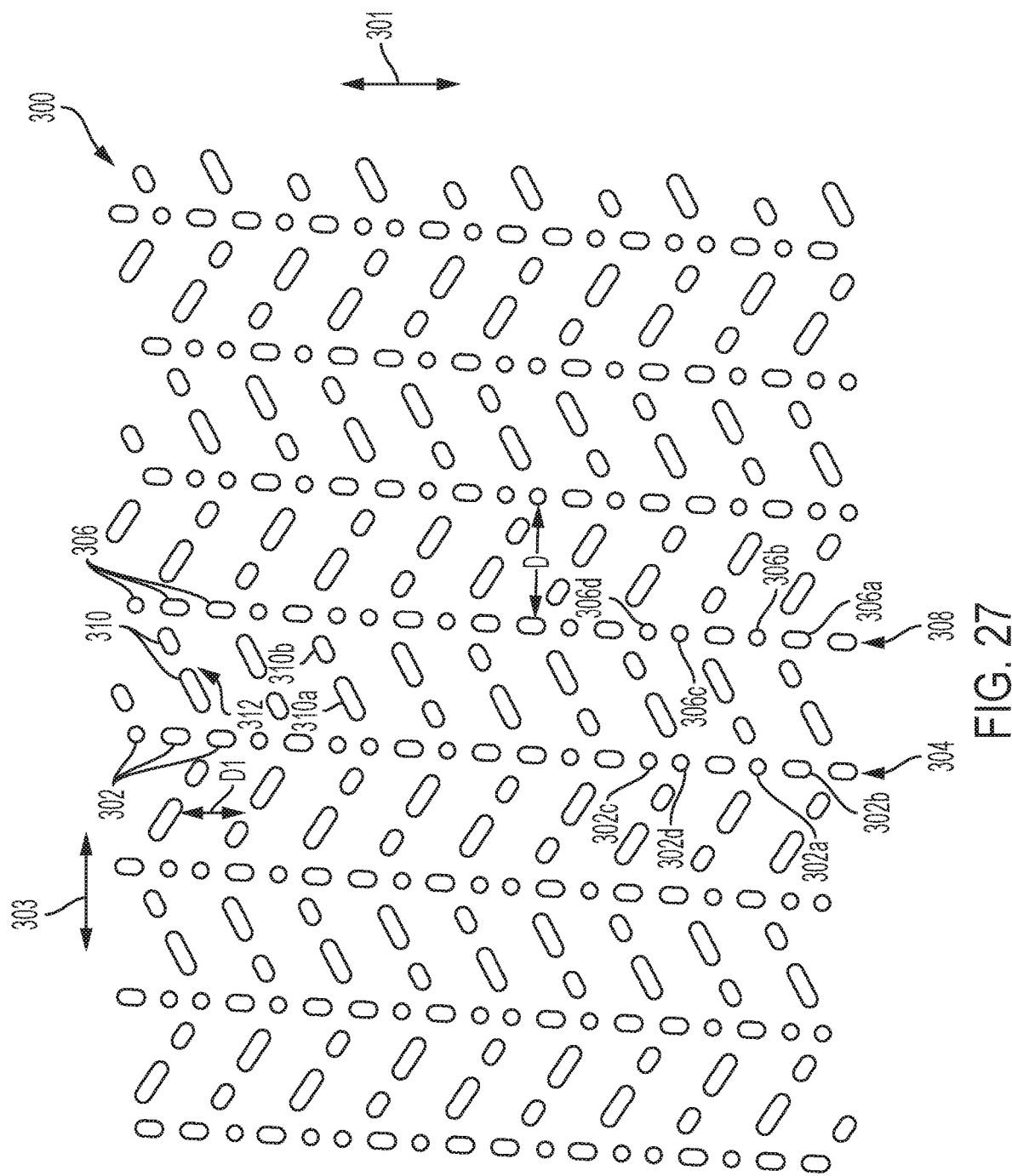
FIGS. 27 and 28 are blown-up examples of discontinuous bond patterns having herringbone patterns.
Figure 28:
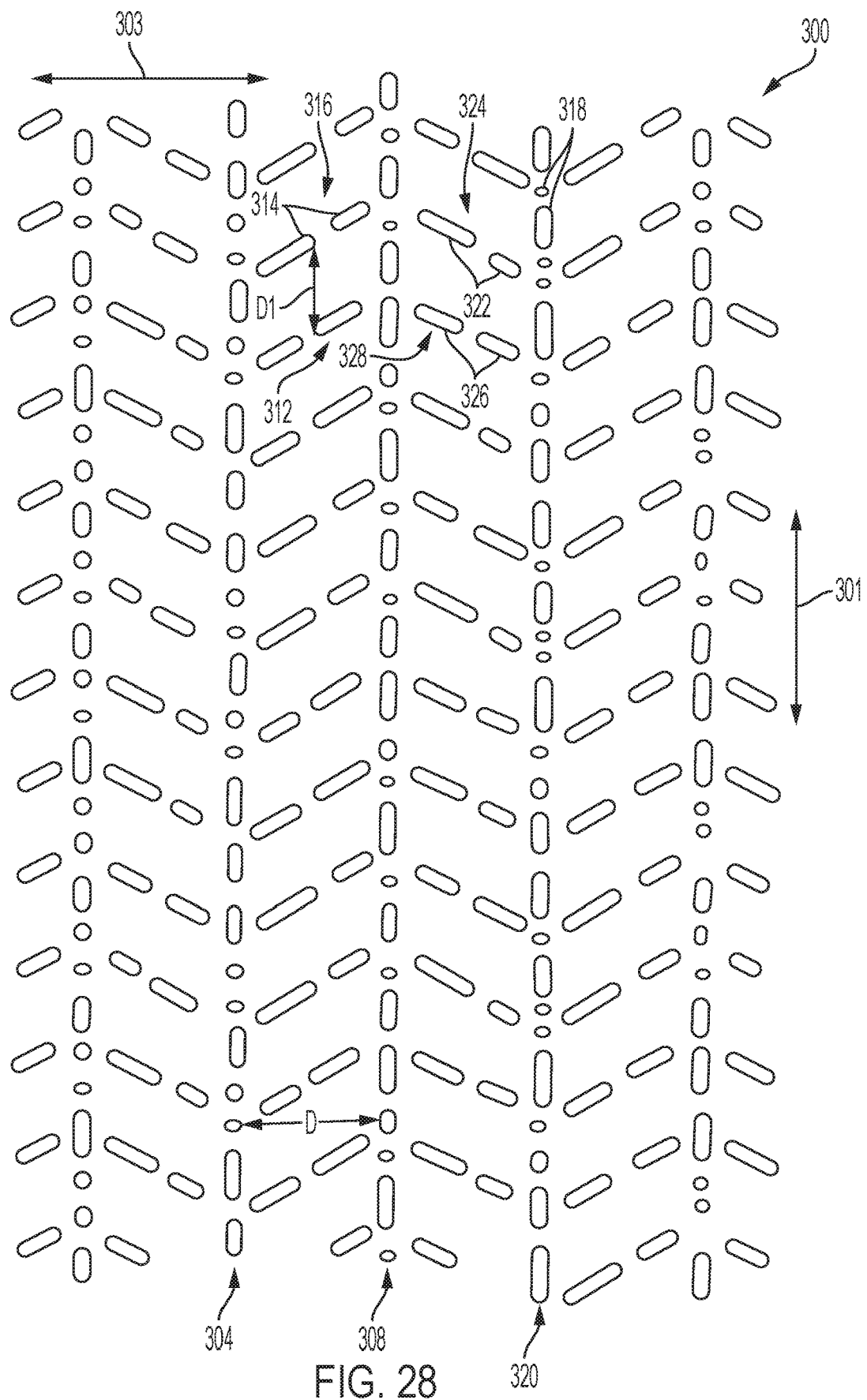

FIG. 27 is an example of a portion of a discontinuous bond or aperture pattern 300 for landing components of absorbent articles, outer cover nonwoven materials of absorbent articles, or other nonwoven absorbent article components. FIG. 28 is an example of a portion of another discontinuous bond or aperture pattern 300 for landing components of absorbent articles, outer cover nonwoven materials of absorbent articles, or other nonwoven absorbent article components. Referring to FIG. 27, the discontinuous bond or aperture pattern 300 may comprise a first plurality of first discontinuous elements 302 forming a first discontinuous line 304. The discontinuous bond or aperture pattern 300 may comprise a second plurality of second discontinuous elements 306 forming a second discontinuous line 308. The discontinuous bond or aperture pattern 300 may comprise a third plurality of third discontinuous elements 310 positioned intermediate the first discontinuous line 304 and the second discontinuous line 308, wherein the plurality of third discontinuous elements 310 form a third discontinuous line 312 that extends in a direction transverse to a direction of extension of the first and second discontinuous lines 304, 308. The third discontinuous line 312 may extend in a direction in the range of about 15 degrees to about 75 degrees, or about 30 degrees to about 60 degrees, relative to the direction of extension of the first and second discontinuous lines 304, 308, specifically reciting all 0.1 degree increments within the specified ranges and all ranges formed therein or thereby. The first discontinuous line 304, the second discontinuous line 308, and the third discontinuous line 312 may all be free of overlap with any portion of each other. In other instances, some portions of the first discontinuous line 304, the second discontinuous line 308, and the third discontinuous line 312 may at least partially overlap. A distance, D, in a direction perpendicular to the first discontinuous line 304, between the first discontinuous line 304 and the second discontinuous line 308 may be in the range of about 2 mm to about 20 mm, about 3 mm to about 15 mm, about 2 mm to about 12 mm, about 3 mm to about 10 mm, about 4 mm to about 8 mm, about 5 mm to about 7 mm, about 6 mm to about 7 mm, or about 6.5 mm, specifically reciting all 0.1 mm increments within the specified ranges and all ranges formed therein or thereby. The first discontinuous line 304 may extend in a direction parallel (accounting for process tolerances), or substantially parallel (e.g., +/−3 degrees) to the second discontinuous line 308.

The first discontinuous elements 302 (any of the first discontinuous elements 302 in the first discontinuous line 304) may comprise a first element 302a and second element 302b that are different in size and/or shape and may comprise a third element 302c and a fourth element 302d that are the same in size and/or shape or substantially the same in size and/or shape (process tolerances). The first discontinuous elements 302 in the first line 304 may also be all the same size and shape, may comprise two or more different sizes and/or shapes, may comprise three and/or more different shapes (see pattern in FIG. 28), may comprise four or more different sizes and/or shapes, or may comprise five or more different sizes and/or shapes, up to 10 different sizes and/or shapes, for example. The second discontinuous elements 306 (any of the second discontinuous elements 306 in the second discontinuous line 308) may comprise a first element 306a and second element 306b that are different in size and/or shape and may comprise a third element 306c and a fourth element 306d that are the same in size and/or shape, or substantially the same in size and/or shape (process tolerances). The second discontinuous elements 306 in the second line 308 may also be all the same size and shape, may comprise two or more different sizes and/or shapes, may comprise three and/or more different shapes (see pattern in FIG. 28), may comprise four or more different sizes and/or shapes, or may comprise five or more different sizes and/or shapes, up to 10 different sizes and/or shapes.

The third discontinuous line 312 may comprise a first element 310a and a second element 310b. The first element 310a and the second element 310b may be the same in size and/or shape, substantially the same in size and/or shape (process tolerances) or may be different in size and/or shape. Although only two third discontinuous elements 310 are illustrated in the discontinuous bond or aperture patterns FIGS. 27 and 28, more than two third discontinuous elements 310 may be used, for example, three or four. The first element 310a may have a positive or a negative slope relative to the central lateral axis 48 of the absorbent article 10 when on the landing component. The second element 310b may have the same positive or negative slope relative to the central lateral axis 48 of the absorbent article 10. In some instances, the first and second elements 310a and 310b may have a slightly different slope (e.g., +/−3 degrees), or a different slope (e.g., +/−10 degrees) relative to the central lateral axis 48. As can be seen in FIGS. 27 and 28, the first and second discontinuous lines 304 and 308 may be longer than the third discontinuous line 312. The first and second discontinuous lines 304 and 308 may both have the same length, or substantially the same length (process tolerances).

Referring to FIG. 28, the discontinuous bond or aperture pattern 300 may comprise a fourth plurality of fourth discontinuous elements 314 forming a fourth discontinuous line 316, wherein the fourth discontinuous line 316 is positioned intermediate the first discontinuous line 304 and the second discontinuous line 312. A distance, D1, between the third discontinuous line 312 and the fourth discontinuous line 316, in a direction parallel to the first and/or second discontinuous lines 304 and 308, may be in the range of about 1 mm to about 12 mm, about 1 mm to about 8 mm, about 1 mm to about 6 mm, about 1.5 mm to about 5 mm, about 2 mm to about 4 mm, or about 3 mm, specifically reciting all 0.1 mm increments within the specified ranges and all ranges formed therein or thereby. The third discontinuous line 312 may or may not extend in a direction parallel to, or substantially parallel to (e.g., +/−1-3 degrees), the fourth discontinuous line 316. The fourth continuous line 316 may have the same features as discussed above with respect to the third discontinuous line 312.

Referring again to FIG. 28, the discontinuous bond or aperture pattern 300 may comprise a fifth plurality of fifth discontinuous elements 318 forming a fifth discontinuous line 320. In the claims, the "fifth" may be referred to as the "fourth" or some other number depending on what order the discontinuous lines or discontinuous elements are being discussed. This may be true for many of the discontinuous elements and the discontinuous lines. The fifth discontinuous line 320 may be the same as the first and second discontinuous lines 304, 308 and may have the same features as discussed above. The discontinuous bond or aperture pattern 300 may comprise a sixth plurality of sixth discontinuous elements 322 forming a sixth discontinuous line 324. The sixth discontinuous line 324 may have the same features as discussed above with respect to the third and fourth discontinuous lines 312 and 316. The sixth discontinuous line 324 may be positioned intermediate the second discontinuous line 308 and the fourth discontinuous line 320 and may extend in a direction transverse to the second and fourth discontinuous lines 308 and 316. The sixth discontinuous line 324 may have the same spacing and angles as discussed above with respect to the third and fourth discontinuous lines 312 and 316.

The discontinuous bond or aperture pattern 300 may comprise a seventh plurality of seventh discontinuous elements 326 forming a seventh discontinuous line 328. The seventh discontinuous line 328 may have the same features as discussed above with respect to the third and fourth discontinuous lines 312 and 316. The seventh discontinuous line 328 may be positioned intermediate the second discontinuous line 308 and the fourth discontinuous line 320 and may extend in a direction transverse to the second and fourth discontinuous lines 308 and 316. The seventh discontinuous line 328 may have the same spacing and angles as discussed above with respect to the third and fourth discontinuous lines 312 and 316.

The sixth and seventh discontinuous lines 324 and 328 may be symmetrical, or substantially symmetrical (process tolerances), to the third and fourth discontinuous lines 312 and 316 about the second discontinuous line 308. Stated another way, the sixth and seventh discontinuous lines 324 and 328 may be a mirror image, or a substantially mirror image (process tolerances) of the third and fourth discontinuous lines 312 and 316 about the second discontinuous line 308.

A number of other lines other than the first, second, third, fourth, fifth, sixth, and seventh discontinuous lines may be part of the discontinuous bond or aperture pattern as illustrated in FIGS. 27 and 28. For brevity, each additional line will not be discussed, but it will be understood that similar looking lines in FIGS. 19, 27, and 28 may have the features discussed herein.

The discontinuous bond or aperture patterns may be positioned on a landing component. The landing component may be an outer cover nonwoven material, a discrete, nonwoven landing zone, or a non-extensible front belt comprising a nonwoven material. The landing component may be configured to receive and hold hooks positioned on tape tabs of fasteners 46. In some instances, the landing component may be positioned in the back waist region and the tape tabs comprising hooks may be positioned in the front waist region if the absorbent article fastens front to back. In other instances, the discontinuous bond or aperture patterns may be positioned on other absorbent article nonwoven components, or on nonwoven materials, for example.

TABLE 1

Figure 29:
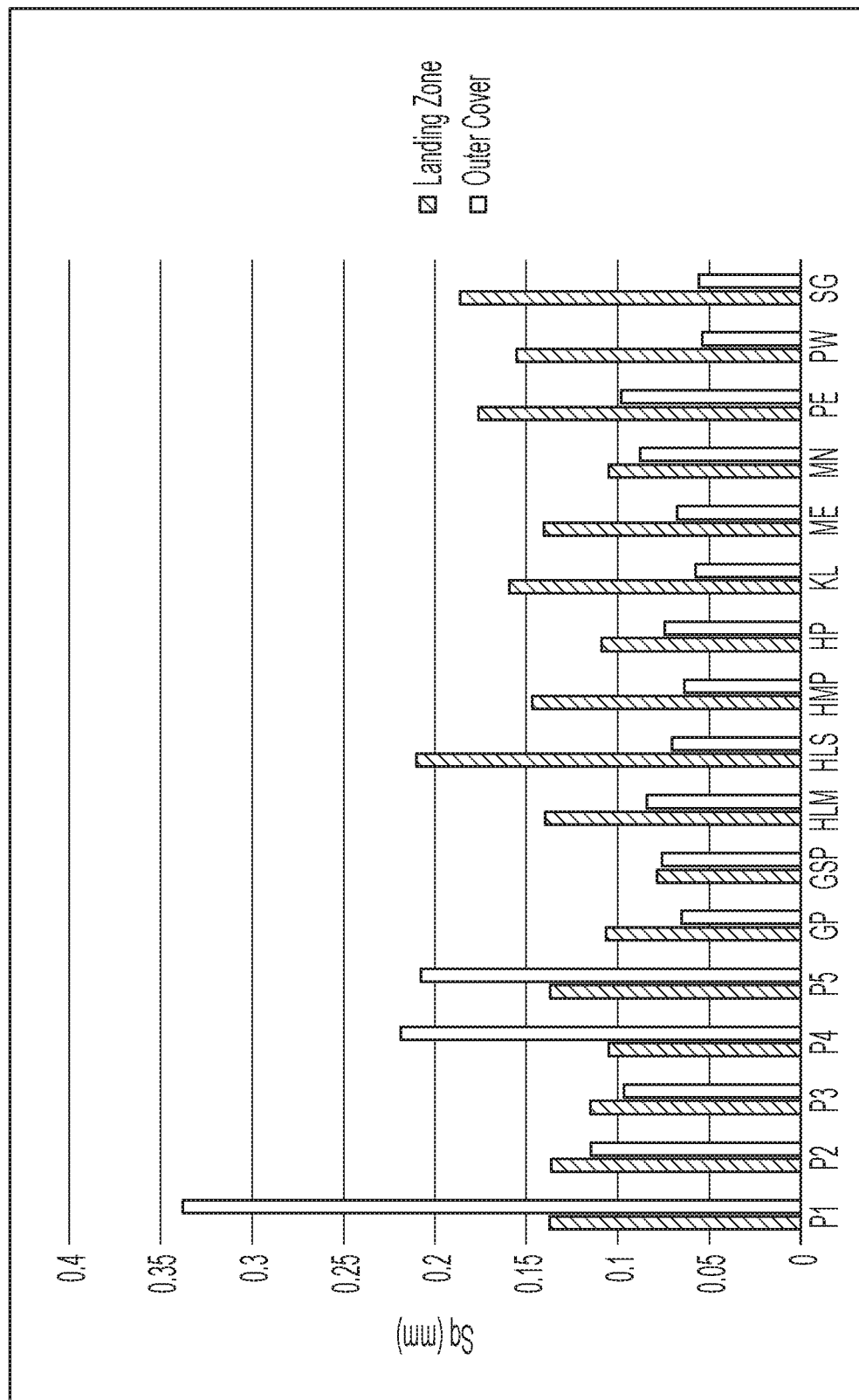
FIG. 29 is a graphical illustration of Sq values (texture) for samples of the present disclosed compared to related art samples.

Present Disclosure Measurements
Table 1 reflects 5 samples for outer cover nonwoven materials and discrete landing zones or discrete, non-elasticized front belts of the present disclosure. These samples were measured for an Sq value (texture) and an Sk value (height), according to the Surface Texture and Height Test herein. The Sq value (texture) data is also reflected in FIG. 29, with the present disclosure sample codes (P1-P5) being represented graphically.

| | Sq (mm) (Texture) | Sk (2-98%) (mm) (Height) |
|---|---|---|
| Outer Cover | | |
| P1—Present Disclosure Sample 1 (Circles Pattern) | 0.338 | 1.197 |
| P2—Present Disclosure Sample 2 (Herringbone Pattern) | 0.115 | 0.484 |
| P3—Present Disclosure Sample 3 (Circles Pattern) | 0.0965 | 0.382 |
| P4—Present Disclosure Sample 4 (Circles Pattern) | 0.219 | 0.875 |
| P5—Present Disclosure Sample 5 (Herringbone Pattern) | 0.208 | 0.738 |
| Discrete Landing Zone or Discrete Non-Elasticized Front Belt | | |
| P1—Present Disclosure Sample 1 (Circles Pattern) | 0.137 | 0.534 |
| P2—Present Disclosure Sample 2 (Herringbone Pattern) | 0.136 | 0.524 |
| P3—Present Disclosure Sample 3 (Circles Pattern) | 0.115 | 0.462 |
| P4—Present Disclosure Sample 4 (Circles Pattern) | 0.105 | 0.429 |
| P5—Present Disclosure Sample 5 (Herringbone Pattern) | 0.137 | 0.529 |

The outer cover nonwoven materials of the present disclosure may have a texture Sq value in the range of about 0.1 mm to about 0.6 mm, about 0.1 mm to about 0.5 mm, about 0.1 mm to about 0.45 mm, about 0.1 mm to about 0.4 mm, about 0.11 mm to about 4 mm, about 0.115 mm to about 0.4 mm, about 0.115 mm to about 0.338 mm, about 0.11 mm to about 0.35 mm, about 0.35 mm, about 0.3 mm, about 0.25 mm, about 0.2 mm, about 0.15 mm, about 0.1 mm, about 0.338 mm, about 0.115 mm, about 0.0965 mm, about 0.219 mm, or about 0.208 mm, specifically reciting all 0.001 mm increments within the specified ranges and all ranges formed therein or thereby. All Sq values are measured according to the Surface Texture and Height Test herein.

The outer cover nonwoven materials of the present disclosure may have a Sk value (height) in the range of about 0.2 mm to about 1.5 mm, about 0.2 mm to about 1.4 mm, about 0.3 mm to about 1.2 mm, about 0.3 mm to about 1.15 mm, about 0.35 mm to about 1.2 mm, about 0.38 mm to about 1.2 mm, about 0.382 mm to about 1.197 mm, about 1.197 mm, about 0.484 mm, about 0.382 mm, about 0.875 mm, or about 0.738 mm, specifically reciting all 0.0001 mm increments within the specified ranges and all ranges formed therein or thereby. All Sk values are measured according to the Surface Texture and Height Test herein.

The discrete landing zone and/or discrete non-elasticized front belt the present disclosure may have a texture Sq value in the range of about 0.05 mm to about 0.4 mm, about 0.08 mm to about 0.3 mm, about 0.9 mm to about 0.3 mm, about 0.1 mm to about 0.3 mm, about 0.1 mm to about 0.2 mm, about 0.1 mm to about 0.15 mm, about 0.115 mm to about 0.338 mm, about 0.137 mm, about 0.136 mm, about 0.115 mm, about 0.105 mm, about 0.137 mm, specifically reciting all 0.0001 mm increments within the specified ranges and all ranges formed therein or thereby. All Sq values are measured according to the Surface Texture and Height Test herein.

The discrete landing zone and/or discrete non-elasticized front belt of the present disclosure may have a Sk value (height) in the range of about 0.2 mm to about 1 mm, about 0.2 mm to about 0.8 mm, about 0.2 mm to about 0.7 mm, about 0.3 mm to about 0.7 mm, about 0.4 mm to about 0.6 mm, about 0.429 mm to about 0.534 mm, about 0.534 mm, about 0.524 mm, about 0.462 mm, about 0.428 mm, or about 0.529 mm, specifically reciting all 0.0001 mm increments within the specified ranges and all ranges formed therein or thereby. All Sk values are measured according to the Surface Texture and Height Test herein.

TABLE 2

Related Art Measurements
Table 2 reflects related art samples for outer covers and discrete landing zone or discrete non-elasticized front belts of the present disclosure. These samples were measured for an Sq value (texture) and an Sk value (height). The Sq data is also reflected in FIG. 29, with the related art sample codes being represented graphically.

| | Sq (mm) (Texture) | Sk (2-98%) (mm) (Height) |
|---|---|---|
| Outer Cover | | |
| GP—Goon Premium, Size S (China) | 0.065 | 0.279 |
| GSP—Goon Super Premium, Size S (China) | 0.076 | 0.349 |
| HLM—Huggies Little Movers, Size 4 (North America) | 0.084 | 0.355 |
| HLS—Huggies Little Snugglers, Size 2 (North America) | 0.070 | 0.291 |
| HMP—Huggies Little Movers Plus, Size 2 (North America) | 0.064 | 0.270 |
| HP—Huggies Platinum, Size S (China) | 0.075 | 0.307 |
| KL—Kirkland Signature, Size 2 (North America) | 0.058 | 0.246 |
| ME—Merries, Size S (China) | 0.068 | 0.294 |
| MN—Moony Natural, Size S (China) | 0.088 | 0.367 |
| PE—Pampers Ichiban, Size S (China) | 0.098 | 0.422 |
| PW—Pampers Cruisers, Size 4 (North America) | 0.054 | 0.226 |
| SG—Seventh Generation Free & Clear, Size 2 (North America) | 0.056 | 0.236 |

TABLE 2-continued

Related Art Measurements
Table 2 reflects related art samples for outer covers
and discrete landing zone or discrete non-elasticized front
belts of the present disclosure. These samples were measured
for an Sq value (texture) and an Sk value (height). The Sq
data is also reflected in FIG. 29, with the related art
sample codes being represented graphically.

| | Sq (mm) (Texture) | Sk (2-98%) (mm) (Height) |
|---|---|---|
| Discrete Landing Zone | | |
| GP—Goon Premium, Size S (China) | 0.107 | 0.515 |
| GSP—Goon Super Premium, Size S (China) | 0.079 | 0.327 |
| HLM—Huggies Little Movers, Size 4 (North America) | 0.140 | 0.508 |
| HLS—Huggies Little Snugglers, Size 2 (North America) | 0.21 | 0.792 |
| HMP—Huggies Little Movers Plus, Size 2 (North America) | 0.147 | 0.588 |
| HP—Huggies Platinum, Size S (China) | 0.109 | 0.419 |
| KL—Kirkland Signature, Size 2 (North America) | 0.159 | 0.623 |
| ME—Merries, Size S (China) | 0.141 | 0.577 |
| MN—Moony Natural, Size S (China) | 0.105 | 0.426 |
| PE—Pampers Ichiban, Size S (China) | 0.176 | 0.689 |
| PW—Pampers Swaddlers, Size 4 (North America) | 0.155 | 0.607 |
| SG—Seventh Generation Free & Clear, Size 2 (North America) | 0.186 | 0.765 |

Repeat Unit Measurements

The various repeat units of the patterns may have certain characteristics, such as repeat unit area (overall X-Y plane area of the repeat unit), repeat unit width, and repeat unit length, for example. Absorbent articles comprising outer cover nonwoven materials and a discrete landing zones or discrete, non-elasticized front belts comprising a repeating pattern of bonds or apertures having a plurality of repeat units may have certain characteristics of the repeat units. Those characteristics are discussed below. Repeat units may also be printed on the outer cover nonwoven materials and the discrete landing zones or the discrete non-elasticized front belts.

Repeat Unit Area-Outer Cover Nonwoven Material

All of, or a majority of, individual repeat units in a repeating pattern of bonds or apertures on an outer cover nonwoven material of an absorbent article may have a repeat unit area in the range of about 25 $mm^2$ to about 400 $mm^2$, about 100 $mm^2$ to about 300 $mm^2$, about 125 $mm^2$ to about 275 $mm^2$, about 150 $mm^2$ to about 250 $mm^2$, about 175 $mm^2$ to about 225 $mm^2$, about 190 $mm^2$ to about 215 $mm^2$, about 195 $mm^2$ to about 210 $mm^2$, about 200 $mm^2$ to about 210 $mm^2$, about 25 $mm^2$ to about 125 $mm^2$, about 25 $mm^2$ to about 100 $mm^2$, about 50 $mm^2$ to about 90 $mm^2$, about 50 $mm^2$ to about 80 $mm^2$, about 55 $mm^2$ to about 75 $mm^2$, about 60 $mm^2$ to about 70 $mm^2$, about 64 $mm^2$, about 65 $mm^2$, or about 66 $mm^2$, specifically reciting all 0.1 $mm^2$ increments within the specified ranges and all ranges formed therein or thereby. Repeat unit areas are measured according to the Repeat Unit Measurement Test herein.

Repeat Unit Area-Discrete Landing Zone or Discrete, Non-Elasticized Front Belt

All of, or a majority of, individual repeat units in a repeating pattern of bonds or apertures on a discrete landing zone or a discrete, non-elasticized front belt of an absorbent article may have a repeat unit area in the range of about 25 $mm^2$ to about 400 $mm^2$, about 40 $mm^2$ to about 300 $mm^2$, about 50 $mm^2$ to about 275 $mm^2$, about 50 $mm^2$ to about 250 $mm^2$, about 50 $mm^2$ to about 225 $mm^2$, about 75 $mm^2$ to about 200 $mm^2$, about 75 $mm^2$ to about 100 $mm^2$, about 150 $mm^2$ to about 225 $mm^2$, about 175 $mm^2$ to about 200 $mm^2$, about 25 $mm^2$ to about 125 $mm^2$, about 25 $mm^2$ to about 100 $mm^2$, about 25 $mm^2$ to about 75 $mm^2$, about 35 $mm^2$ to about 65 $mm^2$, about 40 $mm^2$ to about 60 $mm^2$, about 45 $mm^2$ to about 55 $mm^2$, about 47 $mm^2$, about 48 $mm^2$, or about 49 $mm^2$, specifically reciting all 0.1 $mm^2$ increments within the specified ranges and all ranges formed therein or thereby. Repeat unit areas are measured according to the Repeat Unit Measurement Test herein.

Repeat Unit Width-Outer Cover Nonwoven Material

All of, or a majority of, individual repeat units in a repeating pattern of bonds or apertures on an outer cover nonwoven material of an absorbent article may have a repeat unit width in the range of about 5 mm to about 75 mm, about 5 mm to about 50 mm, about 10 mm to about 40 mm, about 10 mm to about 30 mm, about 10 mm to about 25 mm, about 12 mm to about 22 mm, about 15 mm to about 20 mm, about 16 mm, about 19 mm, about 8 mm to about 20 mm, about 10 mm to about 15 mm, about 12 mm, about 13 mm, or about 14 mm, specifically reciting all 0.1 mm increments within the specified ranges and all ranges formed therein or thereby. Repeat unit widths are measured according to the Repeat Unit Measurement Test herein.

Repeat Unit Width-Discrete Landing Zone or Discrete, Non-Elasticized Front Belt

All of, or a majority of, the individual repeat units in a repeating pattern of bonds or apertures on a discrete landing zone or a discrete, non-elasticized front belt of an absorbent article may have a repeat unit width in the range of about 5 mm to about 75 mm, about 5 mm to about 50 mm, about 8 mm to about 40 mm, about 10 mm to about 30 mm, about 10 mm to about 25 mm, about 10 mm to about 20 mm, about 10 mm to about 18 mm, about 10 mm to about 15 mm, about 15 mm, about 11, about 12, or about 13 mm, specifically reciting all 0.1 mm increments within the specified ranges and all ranges formed therein or thereby. Repeat unit widths are measured according to the Repeat Unit Measurement Test herein.

Repeat Unit Length-Outer Cover Nonwoven Material

All of, or a majority of, the individual repeats units in a repeating pattern of bonds or apertures on an outer cover nonwoven material of an absorbent article may have a repeat unit length in the range of about 2 mm to about 75 mm, about 3 mm to about 50 mm, about 3 mm to about 40 mm, about 5 mm to about 30 mm, about 5 to about 25, about 5 mm to about 20 mm, about 8 mm to about 20 mm, about 11 mm, about 18 mm, about 17 mm, about 3 mm to about 15 mm, about 1 mm to about 15 mm, about 1 mm to about 10 mm, about 1 mm to about 8 mm, about 3 mm to about 10 mm, about 3 mm to about 8 mm, about 3 mm to about 7 mm, about 4 mm, about 5 mm, about 6 mm, or about 7 mm, specifically reciting all 0.1 mm increments within the specified ranges and all ranges formed therein or thereby. Repeat unit lengths are measured according to the Repeat Unit Measurement Test herein.

Repeat Unit Length-Discrete Landing Zone or Discrete, Non-Elasticized Front Belt All of, or a majority of, the individual repeat units in a repeating pattern of bonds or apertures on a discrete landing zone or a discrete, non-elasticized front belt of an absorbent article may have a repeat unit length in the range of about 2 mm to about 75 mm, about 2 mm to about 50 mm, about 3 mm to about 40 mm, about 3 mm to about 30 mm, about 3 to about 25, about 3 mm to about 20 mm, about 3 mm to about 10 mm, about 10 mm to about 20 mm, about 17 mm, about 6 mm, about 7 mm, about 1 to about 10, about 2 mm to about 8 mm, about 2 mm to about 6 mm, about 3 mm to about 5 mm, or about 4 mm, specifically reciting all 0.1 mm increments within the specified ranges and all ranges formed therein or thereby. Repeat unit lengths are measured according to the Repeat Unit Measurement Test herein.

Fuzz

There is a sweet spot for repeat unit size on a component of an absorbent article. A fuzzy looking discrete landing zone, discrete, non-elasticized front belt, and/or outer cover nonwoven material on an absorbent article may not have a premium appearance. The fuzz may be caused by the repeat units being too large. If the repeat units are too small, the nonwoven materials may not look premium. If the repeat units are too large, they may also not look premium as there are too few repeat units on a component. It may be desirable to have large enough repeat units to look premium, but not have the repeat units be so large that there is a lot of un-bonded open space that could create fuzz during consumer usage. The smaller the repeat unit, the lower the chance of fuzzing in un-bonded open spaces. In a discrete landing zone or discrete, non-elasticized front belt context, there may be a need to balance premium appearance with repeat unit size, while still maintaining the repeat unit size small enough to reduce fuzzing and small enough to have fastening strength for being engaged by hooks. Another aspect of premium appearance may be the ability for consumer to see areas that are un-bonded. It is possible to fill in these un-bonded areas with bonds (to reduce fuzz), but it may reduce the premium appearance.

Materials

The discrete landing zones or discrete non-elasticized front belts and the outer cover nonwoven materials of the present disclosure may comprise suitable nonwoven material and/or other materials. Some examples are carded nonwoven materials, air-laid nonwoven materials, wet-laid nonwoven materials, air-through spun nonwovens, spunbond nonwoven materials, spunbond high loft material (e.g., spunbond with at least one layer of crimped fibers), and/or combinations thereof. The nonwoven materials may comprise natural fibers, such as cotton and/or other bio-based materials or resins. The nonwoven materials may be embossed, ultrasonically embossed, hydroentangled, and/or apertured for example. The nonwoven materials may have bonds and three-dimensional features, apertures and three-dimensional features, bonds, apertures, and three-dimensional features, for example.

The discrete landing zones or discrete, non-elasticized front belts and the outer cover nonwovens of the present disclosure may comprise PE/PP bicomponent fiber spunbond nonwoven webs. Other suitable nonwoven webs may comprise spunbond webs comprising side-by-side crimped fibers (e.g., PE/PP or PP/PP) that are bonded via calendar (thermal point) bonding or through-air bonding. Other suitable nonwoven webs may comprise carded, through-air bonded or resin bonded (highloft) nonwovens comprising PE/PP or PE/PET fibers. The nonwoven webs may comprise nanofibers, optionally with other fibers. In some instances, multiple layer webs may be desired over a single layer webs (even at the same basis weight) due to increased uniformity/opacity and the ability to combine webs having different properties. For example, an extensible spunbond nonwoven carrier layer may be combined with a soft, highloft nonwoven (spunbond or carded) to create a nonwoven web that is both soft and strong. The layers may have the same or different surface energy. The layers may have different permeability/capillarity.

Fibers of the discrete landing zones or discrete, non-elasticized front belts and the outer cover nonwovens may comprise any suitable thermoplastic polymers. Example thermoplastic polymers are polymers that melt and then, upon cooling, crystallize or harden, but that may be re-melted upon further heating.

The thermoplastic polymers may be derived from any suitable material including renewable resources (including bio-based and recycled materials), fossil minerals and oils, and/or biodegradeable materials. Some suitable examples of thermoplastic polymers include polyolefins, polyesters, polyamides, copolymers thereof, and combinations thereof. Polypropylene and/or polypropylene copolymers, including atactic polypropylene; isotactic polypropylene, syndiotactic polypropylene, and combination thereof may also be used.

The thermoplastic polymer component may be a single polymer species or a blend of two or more thermoplastic polymers e.g., two different polypropylene resins. As an example, fibers of a first nonwoven layer of a discrete landing zones or discrete, non-elasticized front belts and an outer cover nonwoven may comprise polymers such as polypropylene and blends of polypropylene and polyethylene, while a second nonwoven layer of the discrete landing zones or discrete, non-elasticized front belts and the outer cover nonwoven may comprise fibers selected from polypropylene, polypropylene/polyethylene blends, and polyethylene/polyethylene terephthalate blends. In some forms, a second nonwoven layer may comprise fibers selected from cellulose rayon, cotton, other hydrophilic fiber materials, or combinations thereof.

The fibers of the discrete landing zones or discrete, non-elasticized front belts and the outer cover nonwovens may comprise monocomponent fibers, bi-component fibers, and/or bi-constituent fibers, round fibers or non-round fibers (e.g., capillary channel fibers), and may have major cross-sectional dimensions (e.g., diameter for round fibers) ranging from about 0.1 microns to about 500 microns. The fibers may also be a mixture of different fiber types, differing in such features as chemistry (e.g. polyethylene and polypropylene), components (mono- and bi-), denier (micro denier and >2 denier), shape (i.e. capillary and round) and the like. The fibers may range from about 0.1 denier to about 100 denier.

As used herein, the term "monocomponent fiber(s)" refers to a fiber formed from one extruder using one or more polymers. This is not meant to exclude fibers formed from one polymer to which small amounts of additives have been added for coloration, antistatic properties, lubrication, hydrophilicity, etc.

As used herein, the term "bi-component fiber(s)" refers to fibers which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement where one polymer is surrounded by another, or may be a side-by-side arrangement, a pie arrangement, or an "islands-in-the-sea" arrangement. Some specific examples of fibers which may be used in a nonwoven layer include polyethylene/polypropylene side-by-side bi-component fibers. Another example is a polypropylene/polyethylene bi-component fiber where the polyethylene is configured as a sheath and the polypropylene is configured as a core within the sheath. Still another example is a polypropylene/polypropylene bi-component fiber where two different propylene polymers are configured in a side-by-side configuration. Additionally, forms are contemplated where the fibers of a nonwoven layer are crimped.

Bi-component fibers may comprise two different resins, e.g. a first polypropylene resin and a second polypropylene resin. The resins may have different melt flow rates, molecular weights, or molecular weight distributions.

As used herein, the term "bi-constituent fiber(s)" refers to fibers which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers. In other examples, a bi-component fiber may comprise multiconstituent components.

As used herein, the term "non-round fiber(s)" describes fibers having a non-round cross-section, and includes "shaped fibers" and "capillary channel fibers." Such fibers may be solid or hollow, and they may be tri-lobal, delta-shaped, and may be fibers having capillary channels on their outer surfaces. The capillary channels may be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, TN T-401 fiber is a polyethylene terephthalate (PET polyester).

Bio-Based Content for Absorbent Article Components

Components of the absorbent articles described herein may at least partially be comprised of bio-based content as described in U.S. Pat. Appl. No. 2007/0219521A1. For example, the superabsorbent polymer component may be bio-based via their derivation from bio-based acrylic acid. Bio-based acrylic acid and methods of production are further described in U.S. Pat. Appl. Pub. No. 2007/0219521 and U.S. Pat. Nos. 8,703,450; 9,630,901 and 9,822,197. Other components, for example nonwoven web and film components, may comprise bio-based polyolefin materials. Bio-based polyolefins are further discussed in U.S. Pat. Appl. Pub. Nos. 2011/0139657, 2011/0139658, 2011/0152812, and 2016/0206774, and U.S. Pat. No. 9,169,366. Example bio-based polyolefins for use in the present disclosure comprise polymers available under the designations SHA7260™, SHE150™, or SGM9450F™ (all available from Braskem S.A.).

An absorbent article component may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Nonwoven webs may comprise multicomponent fibers or bicomponent fibers, where at least one or more of the components are bio-based. Examples include side-by-side, sheath/core, or islands in the sea configurations, where one or more or all of the components are bio-based.

Test Methods

Repeat Unit Measurement Test

An absorbent article specimen is taped to a rigid flat surface in a planar configuration with the testing region, such as the outer cover, landing zone, or non-elasticized front belt, of the garment facing surface having a repeating pattern of bonds or apertures facing upward. The article is taped in such way as to avoid introducing distortions of the repeating pattern of apertures due to the extent of longitudinal and lateral extension of the absorbent article. Any absorbent article(s) being tested are conditioned at 23° C.±2° C. and 50%±2% relative humidity for 2 hours prior to testing. For the purposes of this method, all patterns and distances are taken to be based on the projection of the bond or aperture pattern onto a two-dimensional plane.

A single repeat unit (hereafter "SRU") (for subsequent dimensional measurement) within the test region having the repeating pattern of bonds, apertures, or printing comprising the plurality of repeating units is defined as follows. An arbitrary bond, print, or aperture is identified, referred to hereafter as the "chosen point" (hereafter "CP"). Any other bond, print, or aperture in the test region recognized to be in an equivalent position based on the translational symmetry of the repeat units is referred to as an "equivalent point" (hereafter "EP"). The SRU is defined as the set of points that are closer (via Euclidean distance) to the center of the CP than to the center of any other EP in the test region. The SRU identified for measurement must not touch the edge of the test region. After finding all points within the SRU, if it is found that the SRU touches the edge of the test region, this procedure is repeated with an alternative CP. The process is repeated until a SRU that does not touch the edge of the test region is identified.

Figure 30:
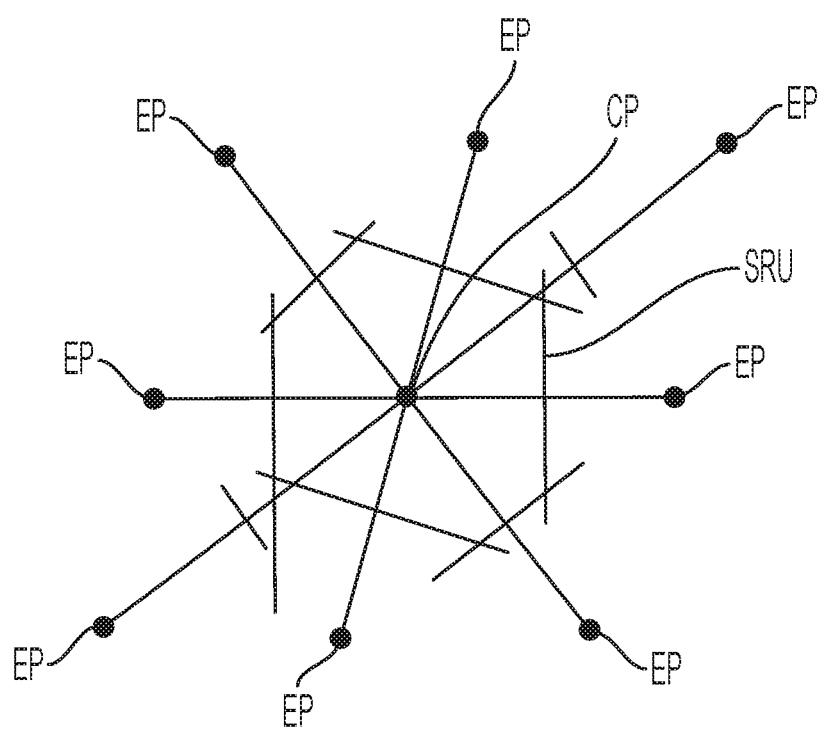
FIG. 30 is an example repeat unit boundary identification linked to the Repeat Unit Measurement Test herein.

One approach to determining the set of points of a SRU is based on identifying a polygonal boundary. Referring to FIG. 30, the boundary of the SRU is the convex polygon formed by the intersection of line segments that immediately border the topsheet region containing the CP. The line segments are identified from lines drawn perpendicular to the midpoint of lines connecting the center of the CP to the center of all neighboring and nearby EP.

Figure 31:
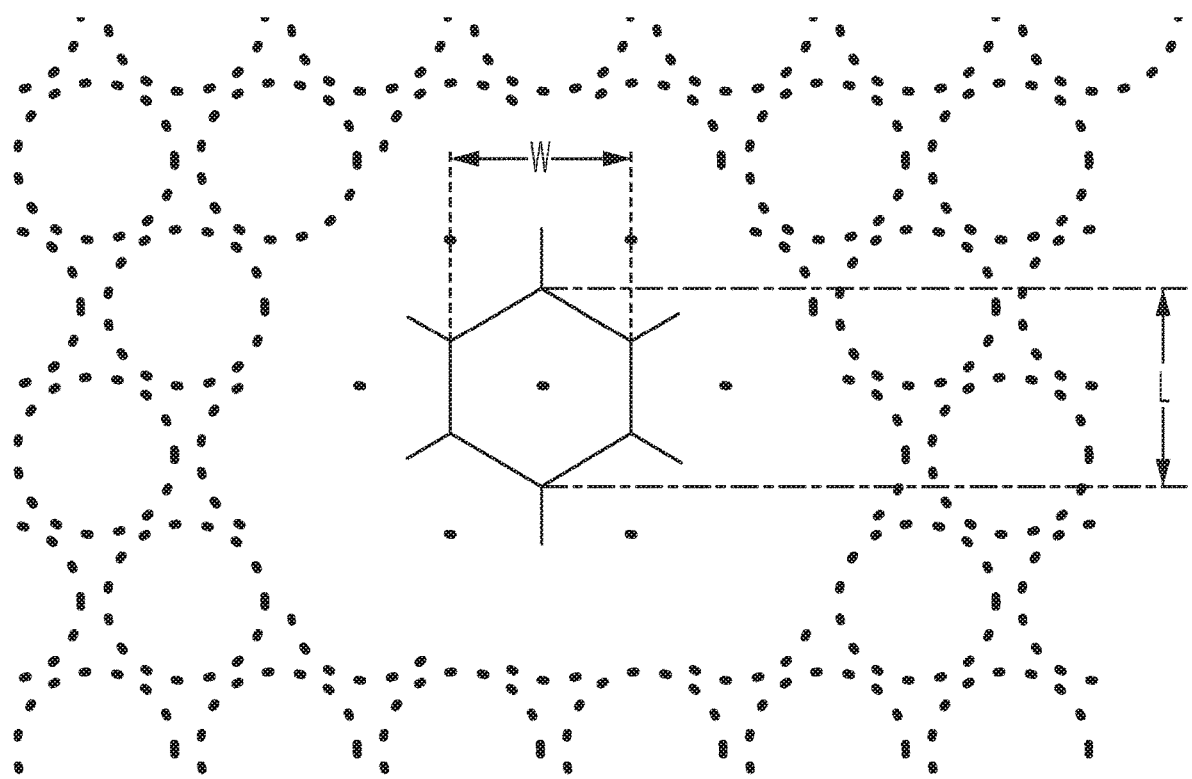
FIG. 31 is an example repeat unit boundary identification taken in a substrate comprising a repeating pattern of apertures, printing, or bonds comprising a plurality of repeat units linked to the Repeat Unit Measurement Test herein.

Referring to FIG. 31, the SRU length (L) is defined as the feret diameter parallel to the longitudinal axis of the absorbent article, and the SRU width (W) is defined as the feret diameter parallel to the lateral axis of the absorbent article. The feret diameter is the distance between two parallel lines, both of which are tangential to the boundary of the SRU, and is recorded to the nearest 0.1 mm.

The interior area of the SRU is recorded to the nearest 0.1 mm$^2$.

Figure 32:
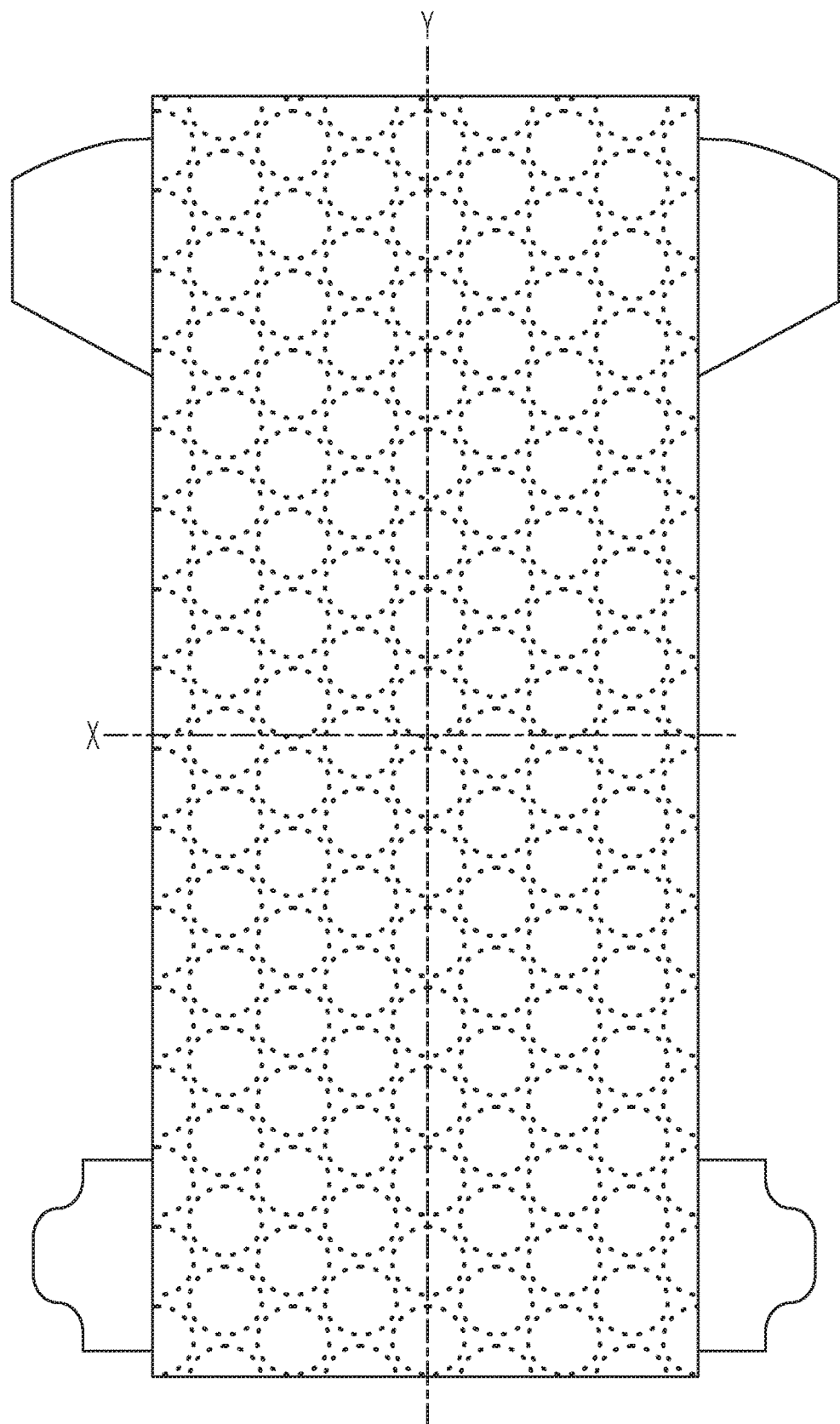
FIG. 32 is an example absorbent article having a topsheet comprising a repeating pattern of apertures, printing, or bonds comprising a plurality of repeat units linked to the Repeat Unit Measurement Test herein.

Referring to FIG. 32, the total lateral width of the absorbent article is measured along the central lateral axis (line X), and is recorded to the nearest 0.1 mm. The total longitudinal length of the absorbent article is measured along the central longitudinal axis (line Y), and is recorded to the nearest 0.1 mm. The total area of the absorbent article is calculated by multiplying the total absorbent article width by the total absorbent article length, and is recorded to the nearest 0.1 mm$^2$.

The number of SRU's per length of the absorbent article is calculated by dividing the total absorbent article longitudinal length by the SRU length and is recorded to the nearest 0.1 SRU's. The number of SRU's per width of the absorbent article is calculated by dividing the total absorbent article lateral width by the SRU width and is recorded to the nearest 0.1 SRU's. The number of SRU's per total area of the absorbent article is calculated by dividing the total absorbent article area (total absorbent article longitudinal length×total absorbent article lateral width) by the SRU area and is recorded to the nearest 0.1 SRU's.

Repeat this procedure on five separate substantially similar absorbent articles and report each of the measurements as the arithmetic mean of the five replicates to the precision described above.

Surface Texture and Height Test

In the Surface Texture and Height Test, a joined backsheet film and outer cover nonwoven material is removed from an absorbent article, and the areal surface topology of nonwoven surface is measured using optical profilometry. The 3D surface data is then processed and analyzed to extract the microscale areal surface roughness parameter Sq (root mean square height) and the surface height parameter Sk. All sample preparation and testing is performed in a conditioned room maintained at about 23±2° C. and about 50±2% relative humidity, and samples are equilibrated in this environment for at least 24 hours prior to testing.

Sample Preparation

To obtain a sample the joined backsheet film and outer cover nonwoven material is removed from an absorbent article. The sample is carefully removed such that its longitudinal and lateral extension is maintained to avoid distortion of the material. A cryogenic spray (such as Cyto-Freeze, Control Company, Houston TX, or equivalent) can be used to remove the sample from the underlying layers, if necessary. Five replicate samples are prepared for testing.

3D Surface Image Acquisition

The sample is adhered in a planar configuration to a rigid flat surface using double sided tape, such that the garment facing surface of the sample is visible. A three-dimensional (3D) surface topography image of the sample is obtained using a DLP-based, structured-light 3D surface topography measurement system (a suitable surface topography measurement system is the MikroCAD Premium instrument commercially available from LMI Technologies Inc., Vancouver, Canada, or equivalent). The system includes the following main components: a) a Digital Light Processing (DLP) projector with direct digital controlled micro-mirrors; b) a CCD camera with at least a 1600×1200 pixel resolution; c) projection optics adapted to a measuring area of at least 60 mm×45 mm; d) recording optics adapted to a measuring area of 60 mm×45 mm; e) a table tripod based on a small hard stone plate; f) a blue LED light source; g) a measuring, control, and evaluation computer running surface texture analysis software (a suitable software is MikroCAD software with MountainsMap technology, or equivalent); and h) calibration plates for lateral (XY) and vertical (Z) calibration available from the vendor.

The optical 3D surface topography measurement system measures the surface height of a sample using the digital micro-mirror pattern fringe projection technique. The nature of this pattern projection technique allows the surface topography of a specimen to be interrogated through a transparent material. The result of the measurement is a 3D data set of surface height (defined as the Z-axis) versus displacement in the horizontal (XY) plane. This 3D data set can also be thought of as an image in which every pixel in the image there is associated an XY displacement, and the value of the pixel is the recorded Z-axis height value. The system has a field of view of 60×45 mm with an XY pixel resolution of approximately 37 microns, and a height resolution of 0.5 microns, with a total possible height range of 32 mm.

The instrument is calibrated according to manufacturer's specifications using the calibration plates for lateral (XY plane) and vertical (Z-axis) available from the vendor.

The sample is placed flat on the table beneath the camera. A 3D surface topology image of the sample is collected by following the instrument manufacturer's recommended measurement procedures, which may include focusing the measurement system and performing a brightness adjustment. No pre-filtering options are used. The collected height image file is saved to the evaluation computer running the surface texture analysis software.

3D Surface Image Analysis

The 3D surface topography image is opened in the surface texture analysis software. The following filtering procedure is then performed on each image: 1) removal of invalid, or non-measured, points; 2) a 5×5 pixel median filter to remove noise; 3) subtraction of the least square plane to level the surface; 4) a Gaussian filter (according to ISO 16610-61) with a nesting index (cut-off wavelength) of 15 mm to flatten the surface (25 mm is to be used for patterns with repeat unit cells with a length or width greater than 15 mm), utilizing end effect correction; and 5) cropping off a 3 mm wide border around the perimeter of the image.

This filtering procedure produces the surface from which the Sq values, as described in ISO 25178-2:2012, are calculated. Record the surface roughness values for Sq to the nearest 0.001 mm. This procedure is repeated for the remaining replicate samples. Average together the 5 replicate Sq measures and report these values to the nearest 0.001 mm.

The surface height measurement is based on the core height value, Sk, parameter described in ISO 13565-2:1996 standard extrapolated to surfaces and ISO 25178-2:2012. The parameter Sk is derived from the Areal Material Ratio (Abbott-Firestone) curve, which is the cumulative curve of the surface height distribution histogram versus the range of surface heights. The core height value is the height difference between the material ratios Mr1 and Mr2 as read off of the Areal Material Ratio curve. Mr1, set to 2%, is the material ratio which separates the protruding peaks from the core roughness region. Mr2, set to 98%, is the material ratio which separates the deep valleys from the core roughness region. Record the surface height Sk value to the nearest 0.001 mm. Average together the five replicate Sk values and report to the nearest 0.001 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. An absorbent article comprising:
a lateral axis;
a front waist region on a first side of the lateral axis;
a back waist region on a second side of the lateral axis;
a liquid permeable topsheet;
a liquid impermeable backsheet;
an absorbent core positioned at least partially intermediate the topsheet and the backsheet;
an outer cover nonwoven material in a facing relationship with the backsheet, wherein the outer cover forms a first portion of a garment-facing surface of the absorbent article; and
a discrete landing zone, wherein the discrete landing zone forms a second portion of the garment-facing surface of the absorbent article;
wherein the outer cover nonwoven material and the discrete landing zone each comprise a pattern on the first and second portions of the garment-facing surface, the pattern comprising:
a repeating pattern of apertures or bonds comprising a plurality of repeat units;
wherein a portion of the pattern within each of the repeat units is substantially the same;
wherein at least some of the repeat units have a repeat unit area in the range of 25 mm$^2$ to 100 mm$^2$, according to a Repeat Unit Measurement Test;
wherein the at least some of the repeat units have a repeat unit width in the range of 5 mm to 30 mm, according to the Repeat Unit Measurement Test;
wherein the at least some of the repeat units have a repeat unit length in the range of 1 mm to 15 mm, according to the Repeat Unit Measurement Test;
wherein the at least some of the repeat units comprise discontinuous bonds;
wherein the discontinuous bonds comprise a first discontinuous line comprising a first plurality of spaced elements, a second discontinuous line comprising a second plurality of spaced elements, a third discontinuous line comprising a third plurality of spaced elements positioned intermediate the first and the second discontinuous lines, and a fourth discontinuous line comprising a fourth plurality of spaced elements; wherein the first discontinuous line extends in a direction substantially parallel to a direction of extension of the second discontinuous line; wherein the third discontinuous line extends in a direction transverse to the first and the second discontinuous lines; wherein the third discontinuous line extends in a direction substantially parallel to a direction of extension of the fourth discontinuous line; wherein the first plurality of spaced elements comprise a first element and a second element that are different.

2. The absorbent article of claim 1, wherein the repeat units have a repeat unit area in the range of 50 mm$^2$ to 80 mm$^2$, according to the Repeat Unit Measurement Test.

3. The absorbent article of claim 1, wherein the repeat units have at least one of a repeat unit width in the range of 5 mm to 20 mm or a repeat unit length in the range of 1 mm to 8 mm, according to the Repeat Unit Measurement Test.

4. The absorbent article of claim 1, wherein the repeating pattern of apertures or bonds comprising the plurality of repeat units forms a herringbone pattern.

5. The absorbent article of claim 1, wherein the outer cover nonwoven material and the discrete landing zone comprise the same pattern on the first, and second portions of the garment-facing surface.

6. The absorbent article of claim 1, wherein the outer cover nonwoven material and the discrete landing zone comprise different patterns on the first and second portions of the garment-facing surface.

7. The absorbent article of claim 1, wherein the first plurality of spaced elements comprise a third element and a fourth element that are the substantially the same.

8. The absorbent article of claim 1, wherein the second plurality of spaced elements comprise a first element and a second element that are different.

9. The absorbent article of claim 8, wherein the second plurality of spaced elements comprise a third element and a fourth element that are substantially the same.

10. The absorbent article of claim 1, wherein the third plurality of spaced elements comprise a first element and a second element that are different.

11. The absorbent article of claim 1, wherein a distance, in a direction perpendicular to the first discontinuous line, between the first discontinuous line and the second discontinuous line is in the range of about 2 mm to about 12 mm.

12. An absorbent article comprising:
a lateral axis;
a front waist region on a first side of the lateral axis;
a back waist region on a second side of the lateral axis;
a liquid permeable topsheet;
a liquid impermeable backsheet;
an absorbent core positioned at least partially intermediate the topsheet and the backsheet;
an outer cover nonwoven material in a facing relationship with the backsheet, wherein the outer cover forms a first portion of a garment-facing surface of the absorbent article;
a discrete landing zone, wherein the discrete landing zone forms a second portion of the garment-facing surface of the absorbent article; and
a first back ear and a second back ear each extending laterally from the back waist region, wherein the first and second back ears form a third portion of the garment-facing surface of the absorbent article;
wherein the outer cover nonwoven material, the discrete landing zone, and the first and second back ear each comprise a herringbone pattern on the first, second, and third portions of the garment-facing surface, the herringbone pattern comprising:
a repeating pattern of bonds comprising a plurality of repeat units;
wherein a portion of the herringbone pattern within each of the repeat units is substantially the same;
wherein the repeat units have a repeat unit area in the range of 25 mm$^2$ to 100 mm$^2$, according to a Repeat Unit Measurement Test;
wherein the repeat units have a repeat unit width in the range of 5 mm to 30 mm, according to the Repeat Unit Measurement Test; and wherein the repeat units have a repeat unit length in the range of 1 mm to 10 mm, according to the Repeat Unit Measurement Test;

wherein the herringbone pattern comprises a first discontinuous line comprising a first plurality of spaced elements, a second discontinuous line comprising a second plurality of spaced elements, a third discontinuous line comprising a third plurality of spaced elements positioned intermediate the first and the second discontinuous lines, and a fourth discontinuous line comprising a fourth plurality of spaced elements; wherein the first discontinuous line extends in a direction substantially parallel to a direction of extension of the second discontinuous line; wherein the third discontinuous line extends in a direction substantially parallel to a direction of extension of the fourth discontinuous line.

13. The absorbent article of claim 12, wherein the repeating pattern of bonds comprising the plurality of repeat units comprises discontinuous bonds.

14. The absorbent article of claim 12, wherein the outer cover nonwoven material comprises a spunbond nonwoven material.

15. An absorbent article comprising:
a lateral axis;
a front waist region on a first side of the lateral axis;
a back waist region on a second side of the lateral axis;
a liquid permeable topsheet;
a liquid impermeable backsheet;
an absorbent core positioned at least partially intermediate the topsheet and the backsheet;
an outer cover nonwoven material in a facing relationship with the backsheet, wherein the outer cover comprises a spunbond nonwoven material and forms a first portion of a garment-facing surface of the absorbent article;
a discrete landing zone, wherein the discrete landing zone forms a second portion of the garment-facing surface of the absorbent article; and
a first back ear and a second back ear each extending laterally from the back waist region, wherein the first and second back ears form a third portion of the garment-facing surface of the absorbent article;

wherein the discrete landing zone and the first and second back ears each comprise a herringbone pattern on the second and third portions of the garment-facing surface, the herringbone pattern comprising:

a repeating pattern of bonds comprising a plurality of repeat units;

wherein a portion of the herringbone pattern within each of the repeat units is substantially the same;

wherein the repeat units have a repeat unit area in the range of 25 $mm^2$ to 100 $mm^2$, according to a Repeat Unit Measurement Test;

wherein the repeat units have a repeat unit width in the range of 5 mm to 30 mm, according to the Repeat Unit Measurement Test; and wherein the repeat units have a repeat unit length in the range of 1 mm to 10 mm, according to the Repeat Unit Measurement Test;

wherein the herringbone pattern comprises a first discontinuous line comprising a first plurality of spaced elements, a second discontinuous line comprising a second plurality of spaced elements, a third discontinuous line comprising a third plurality of spaced elements positioned intermediate the first and the second discontinuous lines, and a fourth discontinuous line comprising a fourth plurality of spaced elements; wherein the first discontinuous line extends in a direction substantially parallel to a direction of extension of the second discontinuous line; wherein the third discontinuous line extends in a direction substantially parallel to a direction of extension of the fourth discontinuous line.

* * * * *